United States Patent
Patel et al.

(10) Patent No.: US 11,974,812 B2
(45) Date of Patent: May 7, 2024

(54) LASER-SPECKLE CONTRAST IMAGING SYSTEM AND METHOD

(71) Applicants: The Medical College of Wisconsin, Inc., Milwaukee, WI (US); Coherence Consulting LLC, Durham, NC (US)

(72) Inventors: Dwani Patel, Milwaukee, WI (US); Al Hafeez Dhalla, Durham, NC (US); Christian B. Viehland, Durham, NC (US); Daniel M. Lipinski, Milwaukee, WI (US)

(73) Assignees: The Medical College of Wisconsin, Inc., Milwaukee, WI (US); Coherence Consulting LLC, Durham, NC (US)

( * ) Notice: Subject to any disclaimer, the term of this patent is extended or adjusted under 35 U.S.C. 154(b) by 0 days.

(21) Appl. No.: 18/550,776

(22) PCT Filed: Mar. 21, 2022

(86) PCT No.: PCT/US2022/021160
§ 371 (c)(1),
(2) Date: Sep. 15, 2023

(87) PCT Pub. No.: WO2022/204034
PCT Pub. Date: Sep. 29, 2022

(65) Prior Publication Data
US 2024/0032790 A1    Feb. 1, 2024

Related U.S. Application Data

(60) Provisional application No. 63/164,209, filed on Mar. 22, 2021.

(51) Int. Cl.
  *A61B 3/12* (2006.01)
  *A61B 3/14* (2006.01)
(52) U.S. Cl.
  CPC .............. *A61B 3/1241* (2013.01); *A61B 3/14* (2013.01)
(58) Field of Classification Search
  CPC .................................. A61B 3/1241; A61B 3/14
  (Continued)

(56) References Cited

U.S. PATENT DOCUMENTS 5,129,400 A * 7/1992 Makino ................... A61B 3/152
                                                600/479
2016/0000324 A1* 1/2016 Rege ..................... A61B 3/0075
                                                600/479

FOREIGN PATENT DOCUMENTS

WO   WO-2018113585 A1 *  6/2018 ........... A61B 3/1025
WO   WO-2022204034 A1 *  9/2022

OTHER PUBLICATIONS

Edmund Optics Worldwide, Techspec 12 mm Dia.×15 mm FL, NIR II Coated, Achromatic Lens, 2023, edmundoptics.com/p/12mm-dia-x-15mm-fl-nir-ii-coated-achromatic-lens/19998/, 2 pages.
(Continued)

*Primary Examiner* — Mohammed A Hasan
(74) *Attorney, Agent, or Firm* — Quarles & Brady LLP; Yakov Sidorin

(57) ABSTRACT

Laser-Speckle Contrast imaging apparatus configured to assess and quantify motion associated with an object and, in a specific case of an eye—retinal vascular anatomy and hemodynamics and generate substantially contrast-free maps of retinal blood flow over a wide field-of-view at up to 590 fps and under short exposure durations (>50 μs), is applicable for diagnosis, study, and management of neurodegenerative conditions (i.e. mild cognitive impairment and Alzheimer's disease) and systemic cardiovascular diseases (i.e. athero- and arteriosclerosis, coronary artery occlusion, and hypertension). The apparatus employs a) a set of apertures substantially blocking light, delivered from a source of light to an illumination arm of the apparatus, from impinging onto an axial point of the front surface of the lens of the illumination arm, and b) polarization gating between the illumination and light-collecting arms of the apparatus. In one implementation, the apparatus is configured to allow for irradiation of the object with an optical field a degree of coherence and/or spectral content of which are varied delivered through the same optical train including the set of apertures.

20 Claims, 10 Drawing Sheets

(58) Field of Classification Search
USPC .................................................. 351/246
See application file for complete search history.

(56) References Cited

OTHER PUBLICATIONS

Edmund Optics Worldwide, Techspec 25 mm Dia.×45 mm FL, NIR II Coated, Achromatic Lens, 2023, edmundoptics.com/p/25mm-dia-x-45mm-fl-nir-ii-coated-achromatic-lens/6250/, 2 pages.
Edmund Optics Worldwide, Techspec 50 mm Dia.×200 mm FL, NIR II Coated, Achromatic Lens, 2023, edmundoptics.com/p/50mm-dia-x-200mm-fl-nir-ii-coated-achromatic-lens/7337/, 2 pages.
Elgendi, On the Analysis of Fingertip Photoplethysmogram Signals, Current Cardiology Reviews, 2012, 8(1):14-25.
Fercher et al., Flow Visualization by Means of Single-Exposure Speckle Photography, Optics Communications, 1981, 37(5):326-330.
Li et al., Advances in Retinal Optical Imaging, Photonics, 2018, 5(2):9, 16 pages.
Parthasarathy et al., Robust Flow Measurement with Multi-Exposure Speckle Imaging, Optics Express, 2008, 16(3):1975-1989.
Patel et al., Validating a Low-Cost Laser Speckle Contrast Imaging System as a Quantitative Tool for Assessing Retinal Vascular Function, Scientific Reports, 2020, 10(1):7177, pp. 1-11.
Postnov et al., Cardiac Pulsatility Mapping and Vessel Type Identification Using Laser Speckle Contrast Imaging, Biomedical Optics Express, 2018, 9(12):6388-6397.
PCT International Search Report and Written Opinion, PCT/US2022/021160, Jun. 13, 2022, 11 pages.

\* cited by examiner

X = 103, Y = -272.6

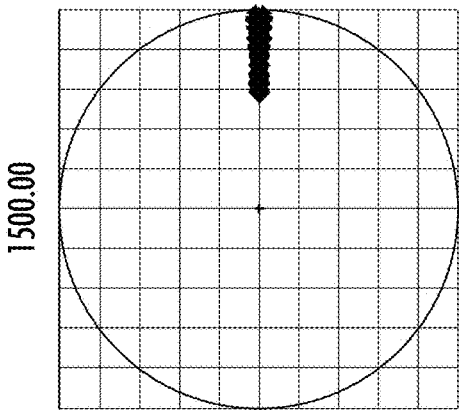

SURFACE 19: PUPIL

| FULL FIELD SPOT DIAGRAM | |
|---|---|
| UNITS ARE μm.    LEGEND ITEMS REFER TO WAVELENGTHS | ZEMAX ZEMAX OPTICSTUDIO 18.9 |
| RMS RADIUS : 562.661 | ILLUMINATION_v2.zmx |
| GEO RADIUS : 754.673 | CONFIGURATION 1 OF 1 |
| CIRCLE DIAM: 1500    REFERENCE : VERTEX | |

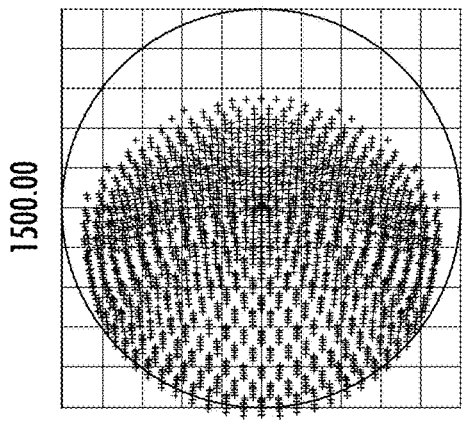

SURFACE 22: ANTERIOR RETINA

| FULL FIELD SPOT DIAGRAM | |
|---|---|
| UNITS ARE μm.    LEGEND ITEMS REFER TO WAVELENGTHS | ZEMAX ZEMAX OPTICSTUDIO 18.9 |
| RMS RADIUS : 449.913 | ILLUMINATION_v2.zmx |
| GEO RADIUS : 728.525 | CONFIGURATION 1 OF 1 |
| CIRCLE DIAM: 1400    REFERENCE : VERTEX | |

FIG. 1C

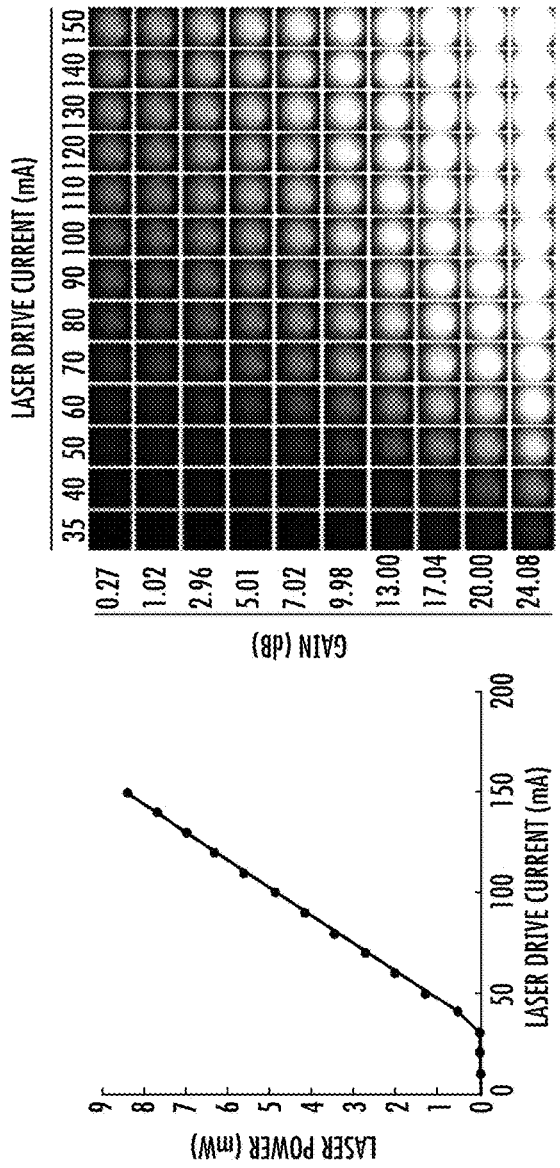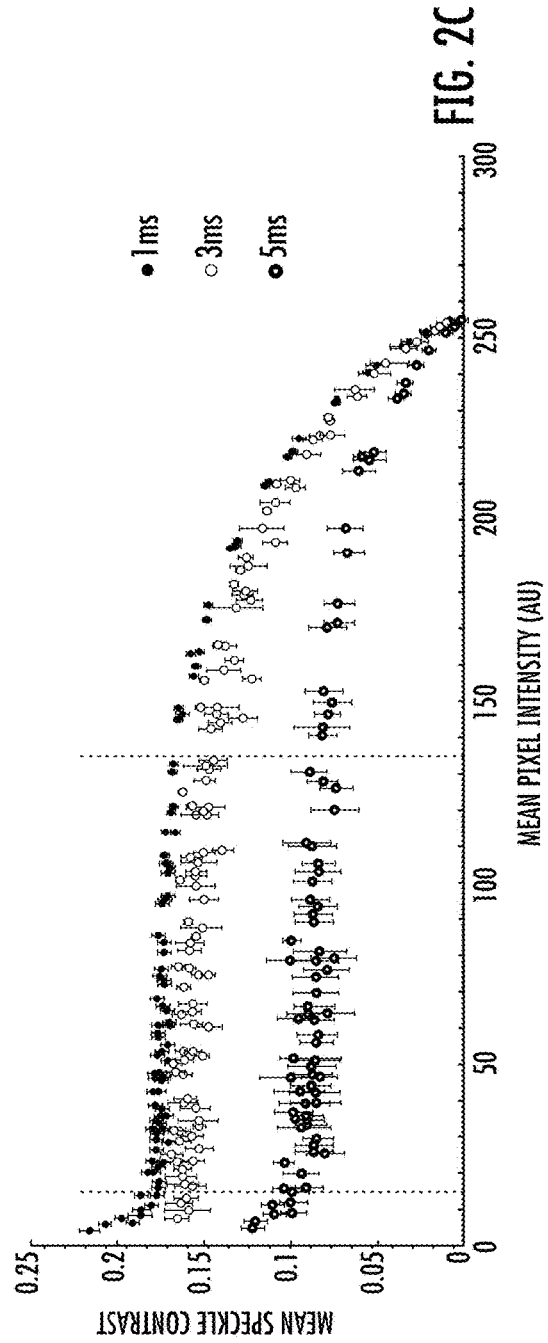
FIG. 2A
FIG. 2B
FIG. 2C

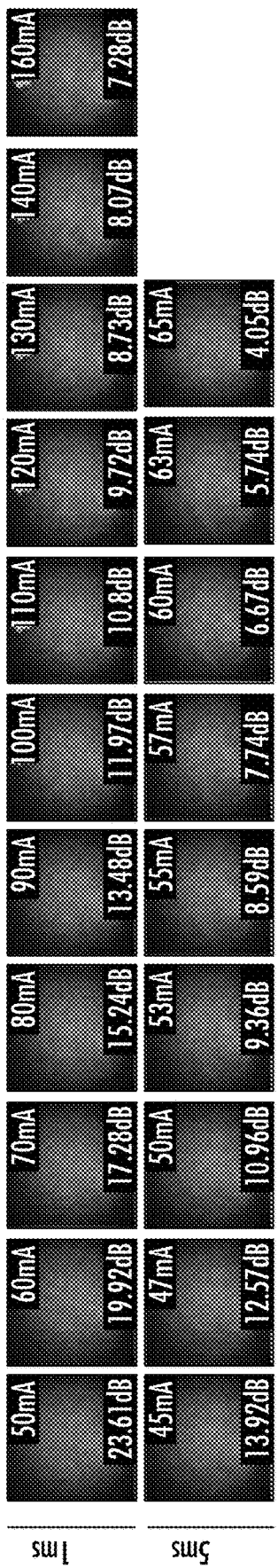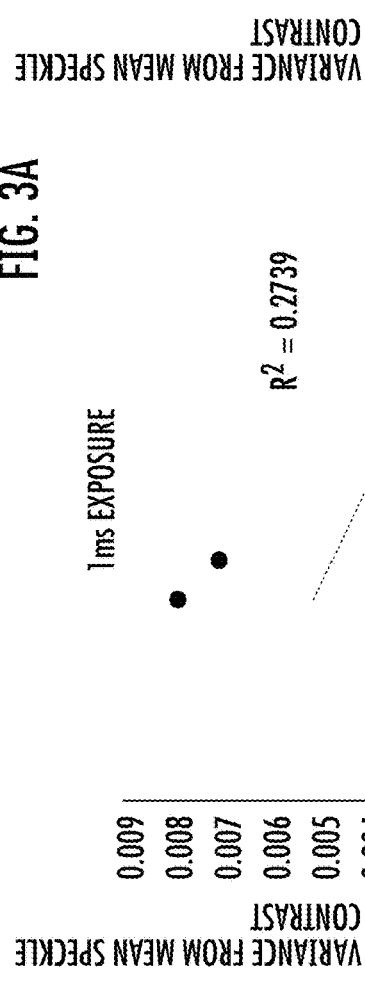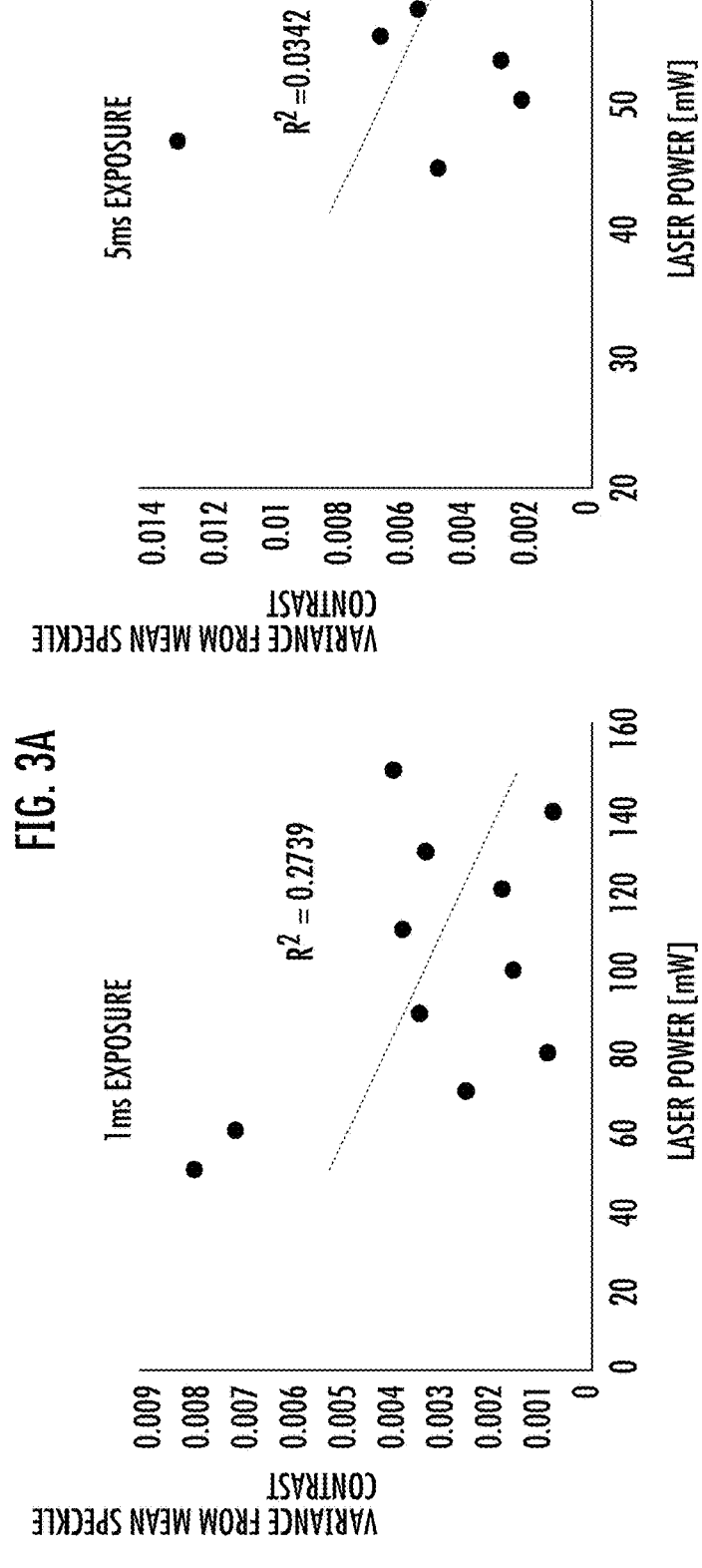
FIG. 3A
FIG. 3B
FIG. 3C

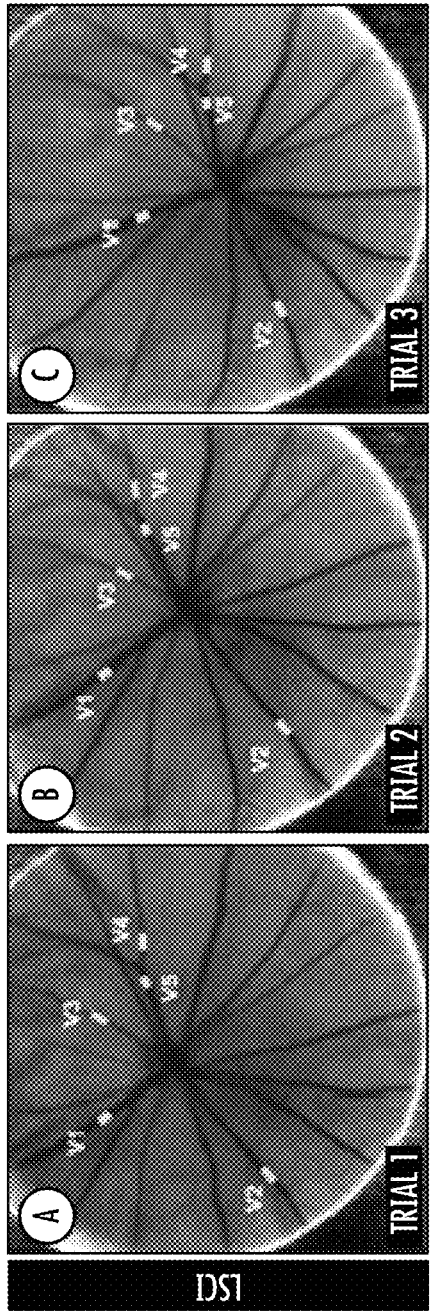
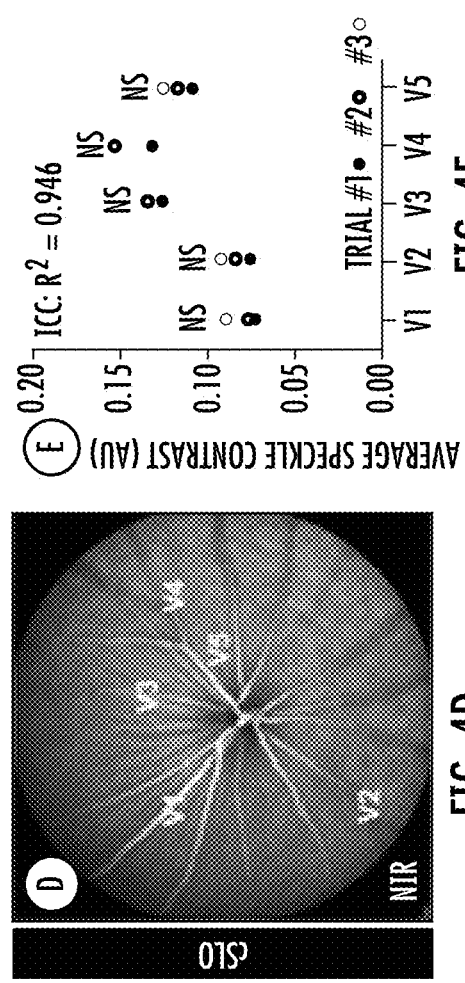
FIG. 4A  FIG. 4B  FIG. 4C  FIG. 4D  FIG. 4E

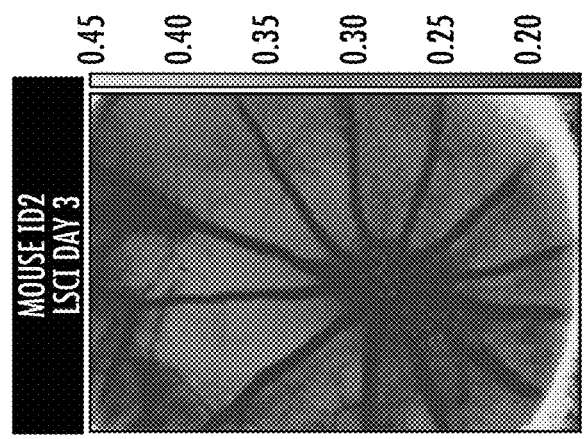
FIG. 5G
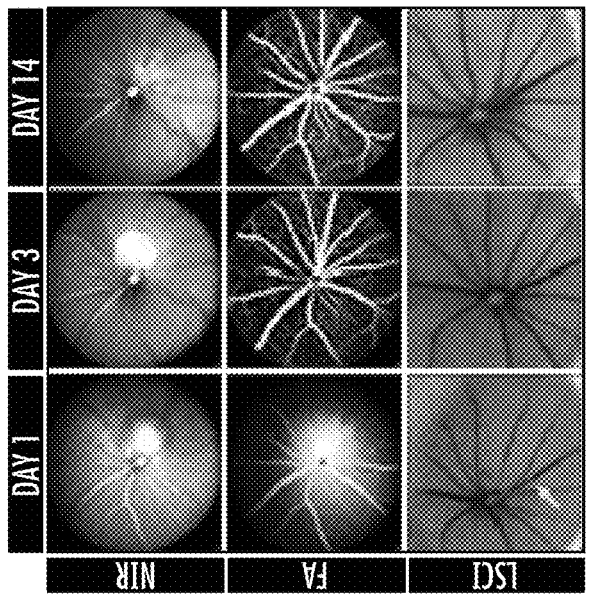
FIG. 5C
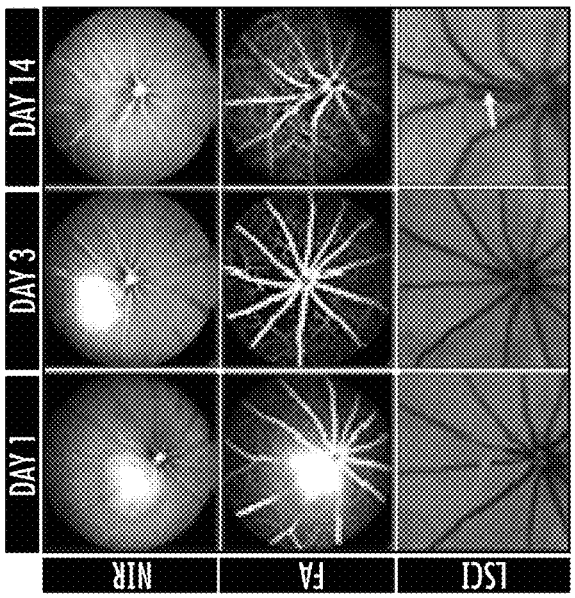
FIG. 5F
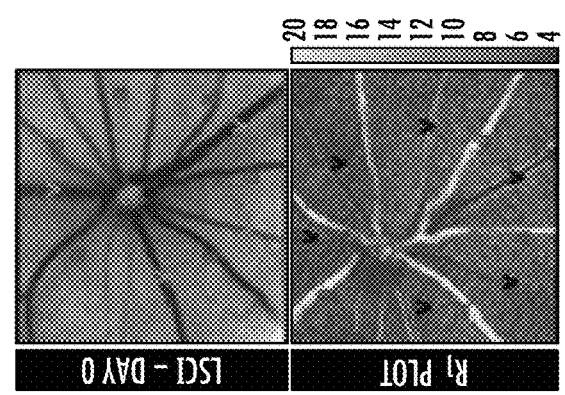
FIG. 5A
FIG. 5B
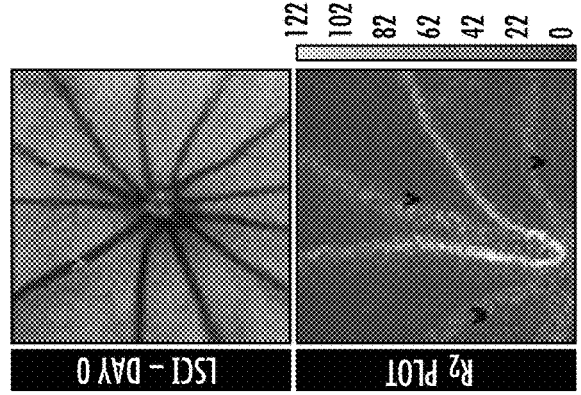
FIG. 5D
FIG. 5E

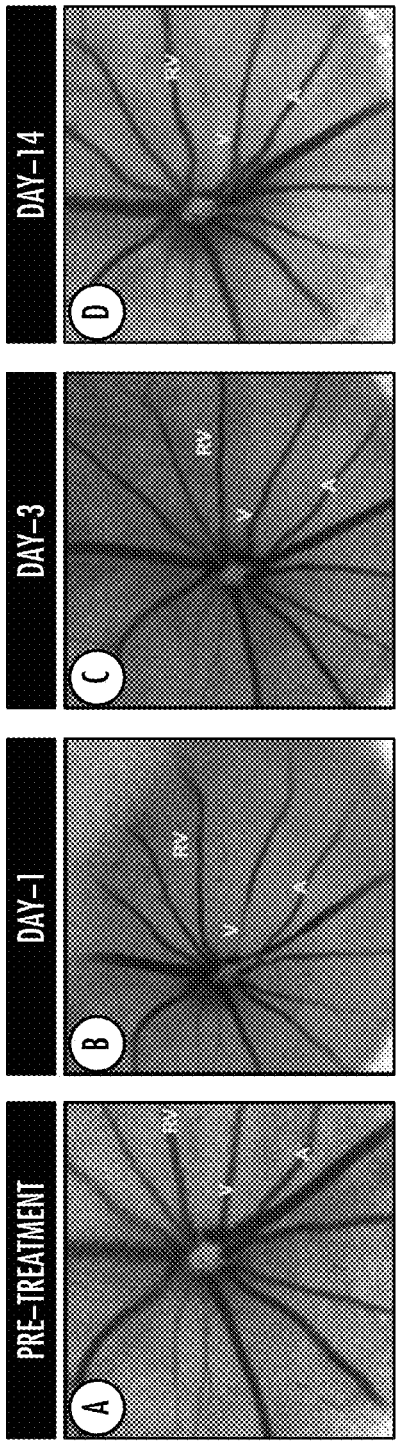
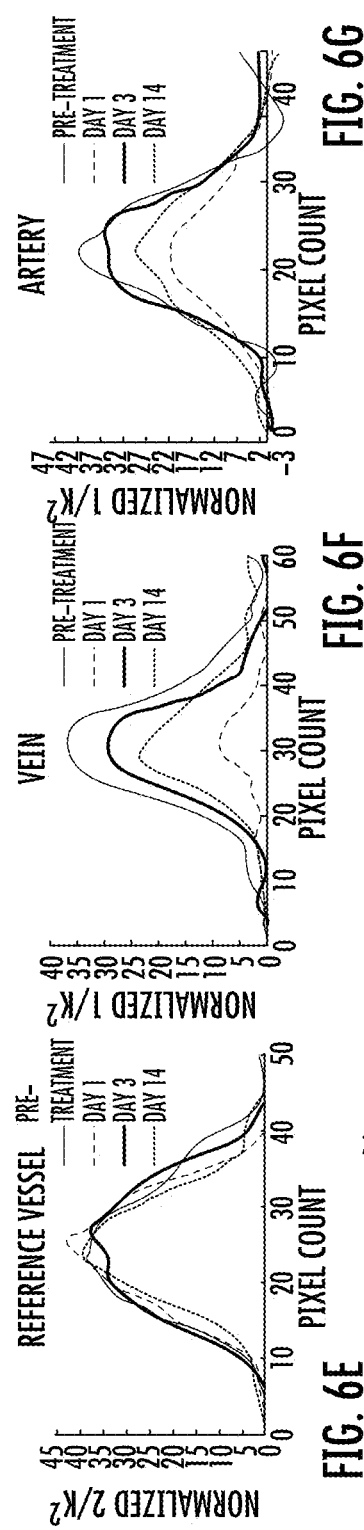
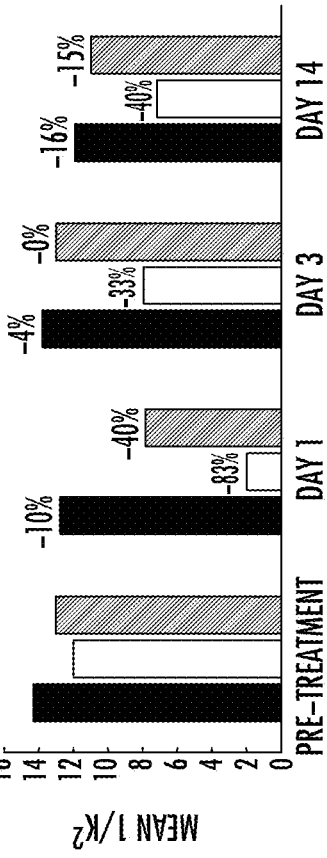

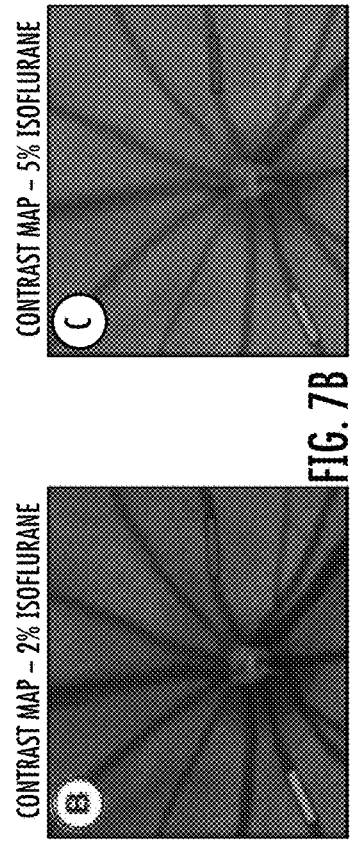
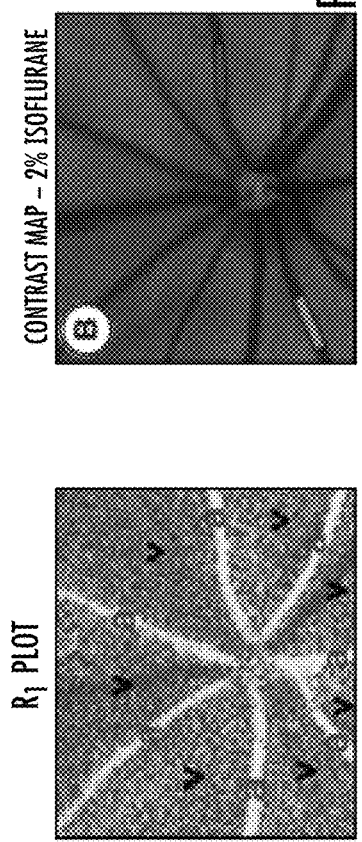
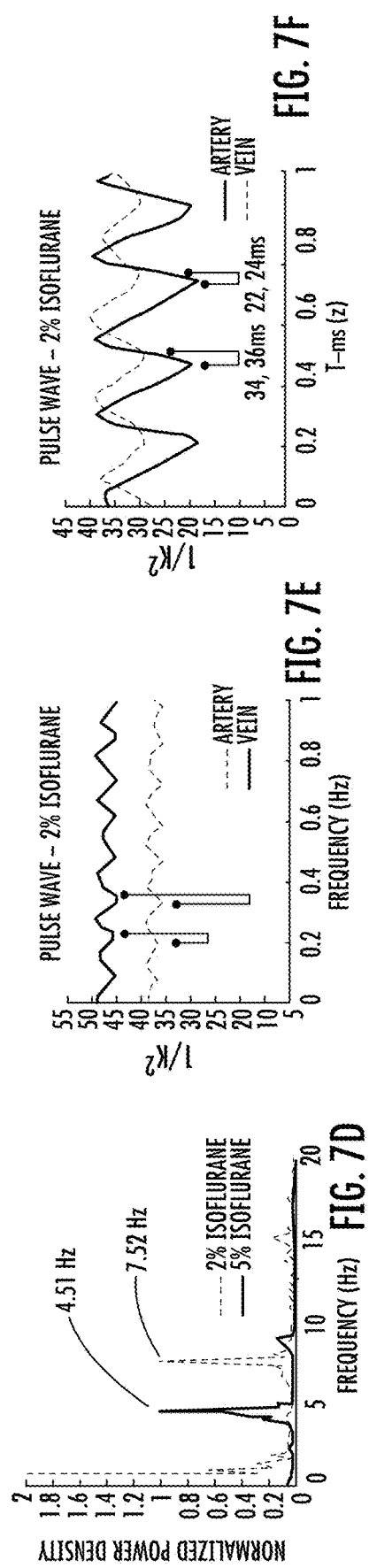
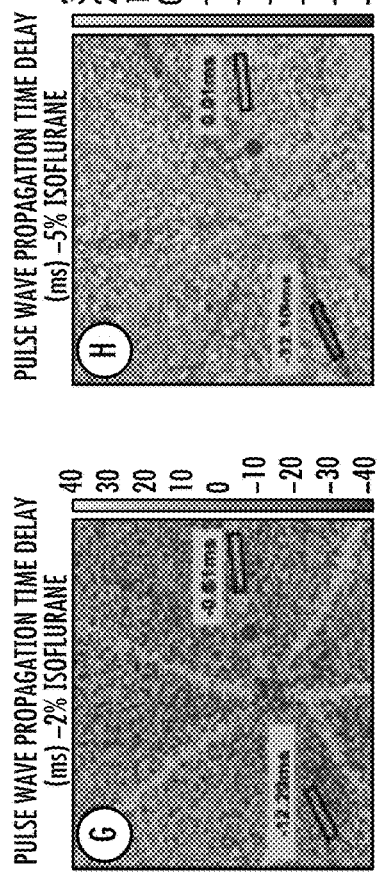

LASER-SPECKLE CONTRAST IMAGING SYSTEM AND METHOD

CROSS-REFERENCE TO RELATED APPLICATIONS

This US patent application is a US National Phase of the International Patent Application No. PCT/US2022/021160 filed on Mar. 21, 2022 and published as WO 2022/204034, which claims priority from and benefit of the U.S. Provisional Patent Application No. 63/164,209 filed on Mar. 22, 2021. The disclosure of each of the above-identified patent documents is incorporated herein by reference.

GOVERNMENT LICENSE RIGHTS TO CONTRACTOR-OWNED INVENTIONS MADE UNDER FEDERALLY SPONSORED RESEARCH AND DEVELOPMENT

This invention was made with government support under research project grant EY027767 awarded by the National Eye Institute. The government has certain rights in the invention.

RELATED ART

The growing worldwide public health burden of sight-threatening retinal disorders—such as diabetic retinopathy (DR), age-related macular degeneration (AMD), and glaucoma—is recognized to necessitate the development of robust diagnostic strategies that enable early intervention. In particular, for diseases with vascular etiology, where the onset of vascular dysfunction precedes the development of vision threatening symptoms, oftentimes by decades, the development of imaging modalities that can identify early biomarkers of disease progression may serve to enhance early detection, guide therapy, and help predict disease outcomes. While the commonly-applied advanced imaging strategies (such as optical coherence tomography (OCT), OCT-angiography, and adaptive optics scanning laser ophthalmoscopy (AO-SLO), for example) have substantially advanced the ability to resolve retinal structures—including the retinal microvasculature—implementation of these strategies largely limited to qualitative assessments of vascular health and function over a small field-of-view.

Doppler-OCT is a technique that enables quantitative velocimetry based on OCT, but this method is highly sensitive to the orientation of the target vessels with respect to the illumination source, complicating its clinical use. Furthermore, the clinical biomarkers observed with the existing imaging modalities have yet to demonstrate strong correlation between anatomy and function, therefore necessitating the development and validation of novel imaging strategies that can detect not only structural changes to the retina, but also quantify physiological variations in response to disease progression or therapeutic intervention.

$$K = \frac{\sigma}{\langle I \rangle} \quad (1)$$

In this regard, laser speckle contrast imaging (LSCI) is a promising, but under-utilized, non-invasive, and non-contact imaging technique capable of generating wide-field maps of blood flow for quantifying retinal hemodynamics, without requiring exogenous contrast. In LSCI, illuminating a rigid surface (e.g., a retinal blood vessel) with light generated by a coherent light source results in the formation of a random 'speckle pattern', where the intensity of each pixel results from the coherent addition of backscattered light with different optical path lengths (see, for example, A. F. Fercher and J. D. Briers, in *Opt. Commun.* 37, 326-330 (1981). Movement within the field-of-view, FOV (e.g., moving blood cells) causes temporal and spatial fluctuations in the speckle pattern such that the rate, at which the intensity of each pixel changes over time, is characterized by the decorrelation time of the speckle autocorrelation function. When this dynamic speckle pattern is recorded over a finite integration time set by the duration of the camera's exposure, the longer integration time relative to the decorrelation time results in a speckle blurring effect (the extent of which is referred to as speckle contrast, K). Speckle contrast K can be quantified as the ratio of the standard deviation of time-integrated speckle intensities to their mean intensity (Eq. 1) within a small spatial window of 5×5 or 7×7 pixels, for example, (referred herein as 'spatial processing') for high temporal resolution, or at the same pixel position across time (referred herein as 'temporal processing') for high spatial resolution.

While the exact relationship between K and the absolute speed (v) of the scattering particle is non-linear, speed may be approximated for simplified LSCI analysis as the inverse square of the speckle contrast (Eq. 2)

$$v \approx \frac{1}{K^2} \quad (2)$$

(see, for example, A. B. Parthasarathy, W. J. Tom, A. Gopal, X. Zhang, & A. K. Dunn, *Opt. Express*, 16, 1975, 2008). Under these principles, and while LSCI has been applied for studying cerebral blood flow, its application for studying retinal hemodynamics (particularly in the context of progressive retinal vascular diseases, such as DR and AMD) remains extremely limited.

Beyond the clinical setting, the development of a LSCI system capable of accurately quantifying early functional changes in retinal hemodynamics may be of great importance in preclinical studies that currently rely on small animal models. For example, while rodents are widely used as models of retinal vascular disease, are recognized in related art to fail to develop clinically-relevant anatomical complications that are characteristic of end-stage human diseases (such as neovascularization, severely limiting their utility for studying disease progression or determining the efficacy of novel therapies). Therefore, the ability to reliably measure early, pre-symptomatic changes in vascular function, prior to the onset of anatomical complications, would serve as both a diagnostic and screening tool for identifying novel biomarkers of disease progression.

The need in a retinal LSCI system configured to characterize anatomical and physiological dysfunction in the context of laser-induced branch retinal vein occlusion (BRVO), and application of such LSCI system to quantification of at least retinal hemodynamics remains not addressed.

SUMMARY

Embodiments of the invention provide a laser-speckle contrast imaging (LSCI) apparatus that includes an optical illumination system and an optical light-collecting system that contains an optical detector and that is operably coupled with the optical illumination system. The optical illumination system has an optical axis and includes a group of lenses and a set of optical apertures dimensioned to deliver light to the group of lenses in transmission of such light through at least of these aperture(s). Each of constituent apertures of the set of optical apertures is (radially) separated from the optical axis by a respectively corresponding non-zero distance. The apparatus may be configured such that, in operation of the apparatus, a first lens surface of the groups of lenses that is immediately neighboring to the set of optical apertures does not receive light from the set of optical apertures at an axial point of such first lens surface. Alternatively or in addition—and substantially in every embodiment of the invention—the set of optical apertures may be defined by an optical fiber component having at least one output optical fiber facet facing the group of lenses. If this is the case, then the apparatus may be configured to satisfy any of the following conditions: 1) at least one output facet of the optical fiber component has an annular cross-section or a crescent-shaped cross-section; and 2) the set of optical apertures is optically conjugated with the at least one output optical fiber facet. Alternatively or in addition—and substantially in any embodiment of the invention, a) the set of optical apertures may include first and second optical aperture areas that are positioned at different azimuthal angles with respect to the optical axis in a plane substantially perpendicular to the optical axis; and/or b) the set of optical apertures may include an array of optical apertures that is curved around the optical axis; and/or c) the set of optical apertures may include an optical aperture shaped as a curved strip; and/or d) the set of optical apertures may be dimensioned to form an optical aperture ring substantially surrounding the optical axis. Alternatively or in addition—and substantially in any embodiment—the optical illumination system may be configured to form, at a target surface, an optical image of the set of optical apertures such that this optical image has an image area that is arcuate and curved around the optical axis and/or the image area that is bound by two curved lines; and/or the image area that is annularly-shaped; and/or the optical light-collecting system may be configured to collect a portion of light (that has been delivered through the set of optical apertures and through the group of lenses to the target surface and that has been reflected by an object surface separated from the group of lenses by the target surface) through an axial region of the target surface that substantially does not overlap with said image area; and/or—in substantially any embodiment—the apparatus may further include a first auxiliary optical lens separated from the set of apertures by the group of lenses (in the latter case, the optical illumination system and the optical light-collecting system share such first auxiliary optical lens).

Alternatively or in addition, and substantially in any implementation of the LSCI apparatus, the optical light-collecting system may be configured to be polarizationally-decoupled from the optical illumination system and/or the apparatus may be equipped with at least a first source of light that is optically and/or physically separated from the group of lenses by the set of optical apertures. In at least one implementation, the set of optical apertures is necessarily formed by an optical fiber component having at least one output optical fiber facet facing the group of lenses.

Alternatively or in addition, and substantially in any implementation of the invention, the apparatus may be equipped with multiple sources of light optically separated from the group of lenses by the set of optical apertures. In this case, a first optical source of such multiple sources of light may be a source of first light having a first degree of coherence, while a second optical source of such multiple sources of light may be a source of second light having a second degree of coherence (here, the first degree of coherence is different from—for example, higher than—the second degree of coherence). In at least one specific case where the apparatus is equipped with multiple sources of light, the set of optical apertures may be defined by an optical fiber component having at least one output optical fiber facet facing the group of lenses; in addition—an input facet of the optical fiber component may be represented by first and second spatially-distinct and not overlapping with one another first and second input facet areas; in addition—the LSCI apparatus may be configured to have the first light from the first source of light be acquired by the optical fiber component only through the first facet area, and second light from the second optical source be acquired by the optical fiber component only through the second facet area, and, in addition—the optical fiber component may be structured to substantially fully spatially overlap the first light and the second light upon propagation through the optical fiber component towards at least one output facet of the optical fiber component to substantially-completely illuminate such output facet of the optical fiber component with either the first light or the second light or both the first and second lights. In at least one specific case where the apparatus is equipped with multiple sources of light, a) the optical fiber component and the first optical source may be configured, as a combination, to ensure that the first light at the at least one output facet of the optical fiber component maintains a degree of coherence that is higher than a pre-determined value despite and regardless of modal dispersion acquired by the first light upon propagation through the optical fiber component; and/or b) the first and second sources of light may be configured to operate either simultaneously or in a time-multiplexed fashion.

Alternatively or in addition, and in multiple not mutually exclusive embodiments of the invention, the optical illumination system may be configured to have at least one of a variable optical parameter or a variable position to alter light distribution of the optical image at the target surface.

Furthermore, embodiments of the invention provide a method that includes a step of forming, at a chosen target surface, an optical image of the set of optical apertures in first illuminating light delivered to the target surface through the set of optical apertures and through the group of lenses of the optical illumination system of one of the embodiments of the LSCI apparatus identified above such that the optical image has an image area that is arcuate and curved around the optical axis and/or bound by two curved line and/or annularly-shaped. The method additionally includes a step of transmitting a portion of the first illuminating light from an object surface (that is separated from the optical illumination system by the target surface) towards an optical lens of the optical light collecting system of the LSCI apparatus through a designated area of the target surface while not transmitting this portion of the first illuminating light through the image area. At this step, the portion-at-hand of the first illuminating light is formed by the illuminating light reflected at the object surface. The method additionally includes a step of forming at least one optical image of the object surface at an optical detector of the optical light-collecting system of the apparatus.

In at least one implementation of the method, the step of forming the optical image of the set of optical apertures may include receiving (by the group of lenses of the optical illumination system) of the first illuminating light having a first state of polarization, while the step of transmitting the portion of the first illuminating light from the object surface may include includes transmitting a portion of the first illuminating light that has a second state of polarization (here, the first state of polarization and the second state of polarization are different from one another). In at least one implementation, the method may additionally include a step of mutually aligning the optical illumination system and the target surface by transmitting, through the set of optical apertures, second illuminating light. When this is the case, a first optical parameter of the first illuminating light and a respectively-corresponding second optical parameter of the second illuminating light are different from one another. These first and second optical parameters may include, respectively, first and second optical wavelength and/or first and second degrees of coherence, to name just a few. When the first and second optical parameters represent corresponding degrees of coherence of light, the first degree of coherence may be chosen to be different from—for example, higher than—the second degree of coherence.

Alternatively or in addition- and substantially in every implementation of the method—the method may include a step of transmitting the first illuminating light through the at least one output facet, of the optical fiber component, which output facet is dimensioned as a ring and is defined in a surface transverse to an axis of the optical fiber element. Alternatively or in addition—and substantially in every implementation of the method—the step of transmitting the portion of the first illuminating light through the designated area of the target surface includes transmitting said portion of the first illuminating light through a surface area, of the target surface, that is fully encircled by the image area of the optical image of the set of optical apertures.

In at least some of implementations of the method that employ the use of the optical fiber component, the method may further include at least one of a) coupling the first illuminating light having a first optical parameter into an optical fiber component (which component is configured to define the set of optical apertures) only through a first input facet area of the optical fiber component, and b) coupling a second illuminating light having a second optical parameter into the same optical fiber component but only through a second input facet area of the optical fiber component. Here, the first and second input facet areas of the optical fiber component do not overlap with one another, and the first and second optical parameters differ from one another. In one specific case of the latter, the first and second optical parameters may include, respectively, first and second degrees of coherence and/or first and second optical wavelengths; and—alternatively or in addition—the method may include a step of substantially-completely illuminating at least one output facet of the optical fiber component with at least one of the first illuminating light and the second illuminating light. Alternatively or in addition—and substantially in any embodiment of the method that employs processes of coupling if the first and second illuminating light—such coupling of the first illuminating light and such coupling of the second illuminating light may be carried out either simultaneously or in a time-multiplexed fashion.

Alternatively or in addition, an embodiment of the method may additionally include a step of determining an index of motion at the object surface (for example, with the use of a programmable data-processing electronic circuitry, operably connected with the optical detector) based at least in part on a speckle contrast characteristic of at least such optical image of the object surface formed with the use of the optical light-collecting system. Here, at least in one case, the object surface may be chosen to be represented by a surface of a biological tissue, in which case the index of motion may be a parameter of a blood flow in such biological tissue; and/or the object surface may be chosen to be represented by a surface of the retina of an eye, in which case the step of determining an index of motion may include i) determining a blood flow rate in a reference blood-vessel in the retina from at least the optical image of the object surface; and generating a visually-perceivable output representing quantified changes in retinal hemodynamics over a predetermined period of time based at least on such determining; and/or ii) determining at least one of cardiac parameters including systolic peak amplitude, crest time, diastolic peak amplitude, time to diastolic peak, time to closure of an aortic valve, time between systolic and diastolic peaks, and augmentation index based on at least such optical image; and generating a visually-perceivable output representing said at least one of cardiac parameters.

Embodiments of the invention additionally provide use of the LSCI apparatus identified above in an imaging process employing fluorescence and/or use of such apparatus to obtain spectroscopic information about the object surface without establishing contact with such object surface and/or use of such apparatus to optically determine a degree of blood oxygenation in a biological tissue without establishing contact with such biological tissue.

BRIEF DESCRIPTION OF THE DRAWINGS

For a more complete understanding of the disclosure, reference is made to the following detailed description and accompanying Drawings, of which:

FIGS. 1B and 1C provide spot diagrams representing light distribution at the pupil of an eye and at the retina, respectively, when these surfaces are illuminated with light from the source of light delivered to the lens portion of the optical illumination system of the embodiment of FIG. 1A only through one of the multiple distal ends of the optical fiber element of the embodiment.

FIGS. 2A, 2B, and 2C present results of assessment of the Effect of Mean Pixel Intensity on Mean Speckle Contrast. Laser power output (mW) can be controlled by adjusting the drive current (mA) applied to the laser diode (FIG. 2A). A rigid surface was placed 2 cm orthogonally from the tip of the imaging bore and LSCI was performed at 3 ms exposure durations at 170 fps while varying drive current (35 mA-150 mA) and gain (0.27 dB-24.08 dB) to alter mean pixel intensity (0-255 AU) of the raw speckle images (FIG. 2B). LSCI was repeated with 1 ms and 5 ms exposure durations. For each of the 390 combinations of imaging parameters evaluated, the mean speckle contrast across 25 temporally processed frames (N=12 sets) was plotted against the mean pixel intensity measured across their corresponding raw speckle images (FIG. 2C).

FIGS. 3A, 3B, and 3C Illustrate optimization of Imaging Parameters such as Gain and Laser Power. At any fixed exposure duration, the same mean pixel intensity (0-255 AU) can be achieved by altering laser power or gain. For example, for any of the 11 different combinations of drive current and gain settings at 1 ms exposure and 9 different combinations at 5 ms, we achieve a target mean pixel intensity of 100 AU with minimal variance (±0.34 AU at 1 ms; ±0.30 AU at 5 ms) (FIG. 3A). Variance from the mean speckle contrast measured across all 11 imaging conditions under 1 ms exposure duration (FIG. 3B) and all 9 imaging conditions under 5 ms exposure duration (FIG. 3C) are plotted against laser power. Regression analysis shows weak negative correlation between variance from mean speckle contrast and laser power at 1 ms and 5 ms exposure durations ($R^2=0.2739$ and $R^2=0.034$, respectively).

FIGS. 4A, 4B, 4C, 4D, 4E address Repeatability of Speckle Contrast Measurements In Vivo. LSCI was performed at 170 fps, 2.5 ms exposure duration, and f/16 in a murine eye across three imaging sessions (FIGS. 4A, 4B, 4C). A representative near infrared (NIR) image of the retina was acquired on a confocal scanning laser ophthalmoscope (cSLO) (FIG. 4D). Average speckle contrast (FIG. 4E) was measured in each of 5 vessel ROIs and an intra-rater reliability study demonstrates an intraclass correlation coefficient of 0.946 between speckle contrast measurements within the same retinal vessel ROI across various imaging sessions.

FIGS. 5A, 5B, 5C, 5D, 5E, 5F, and 5G illustrate Murine Branch Retinal Vein Occlusion (BRVO). BRVO was performed in murine retinae to demonstrate the ability of LSCI to detect pathological alterations in blood flow and retinal vascular anatomy. LSCI was performed in Mouse ID1 (FIG. 5A) and Mouse ID2 (FIG. 5D) one day prior to BRVO (170 fps, 2.5 ms exposure, and f/16). Fourier analysis was applied to segment retinal veins (v) from retinal arteries (a) (FIGS. 5B, 5E). Both mice were followed for 14 days following BRVO with near infrared (NIR) imaging, fluorescein angiography (FA), and LSCI (FIGS. 5C, 5F). Vein occlusion (red arrow) and vessel stenosis with distal dilation (yellow arrow) is evident from LSCI (FIG. 5C). Likewise, LSCI reveals vessel stenosis (blue arrow), as well as increased tortuosity (green arrow) and increased vessel thickness (white arrow) (FIG. 5F). A color map (FIG. 5G) of the speckle contrast image obtained at Day 3 in Mouse ID2 reveals increased speckle contrast in areas of the retina which are hypo-perfused, correlating with the areas of hypo-perfusion observed via FA (FIG. 5F).

FIGS. 6A, 6B, 6C, 6D, 6E, 6F, 6G, and 6G illustrate assessing Flow Profiles Across Retinal Vessels following BRVO. Speckle contrast derived flow rates ($1/K^2$) relative to background are assessed across several retinal vessels prior to laser-induced BRVO, and then 1,3, and 14 days following BRVO (FIGS. 6A through 6D). Shown are relative flow profiles across a reference vessel (RV), outside of the laser treatment site, as well as a retinal vein (V) and retinal artery (A) within the treatment site (FIGS. 6E through 6G). The mean inverse speckle contrast, determined by the mean area under the curve, was measured across RV, V, and A before and then 1, 3, and 14 days post BRVO. Percent change in mean flow rate is shown relative to flow rates measured prior to laser treatment (FIG. 6H).

FIGS. 7A, 7B, 7C, 7D, 7E, 7F, 7G, and 7H: Evaluating Cardiac Function with LSCI. LSCI was performed in a murine retina at 376.2 fps, 2.5 ms exposure, and f/16. Fourier analysis was performed to segment retinal veins (v) from arteries (a) (FIG. 7A). LSCI was subsequently performed under 2% isoflurane anesthesia (FIG. 7B) and 5% isoflurane anesthesia (FIG. 7C). Fourier analysis was applied to measure change in heart rate under 2% isoflurane (451.2 bpm) and 5% isoflurane (270.6 bpm) (FIG. 7D). Mean speckle contrast was measured in the arterial (red) and venous (blue) ROIs drawn in FIGS. 7B, 7C to plot variation in speckle contrast over time under 2% isoflurane (FIG. 7E) and 5% isoflurane (FIG. 7F). The time delay between pulse wave propagation from retinal artery to retinal vein is highlighted in FIGS. 7E through F. Fourier analysis is applied to create a map pulse wave propagation time delay over the entire field-of-view under 2% isoflurane (FIG. 7G) and 5% isoflurane (FIG. 7H). Time delay measurements in FIGS. 7G through H are relative to time measured in each respective, red circular ROI.

Figure 1A:
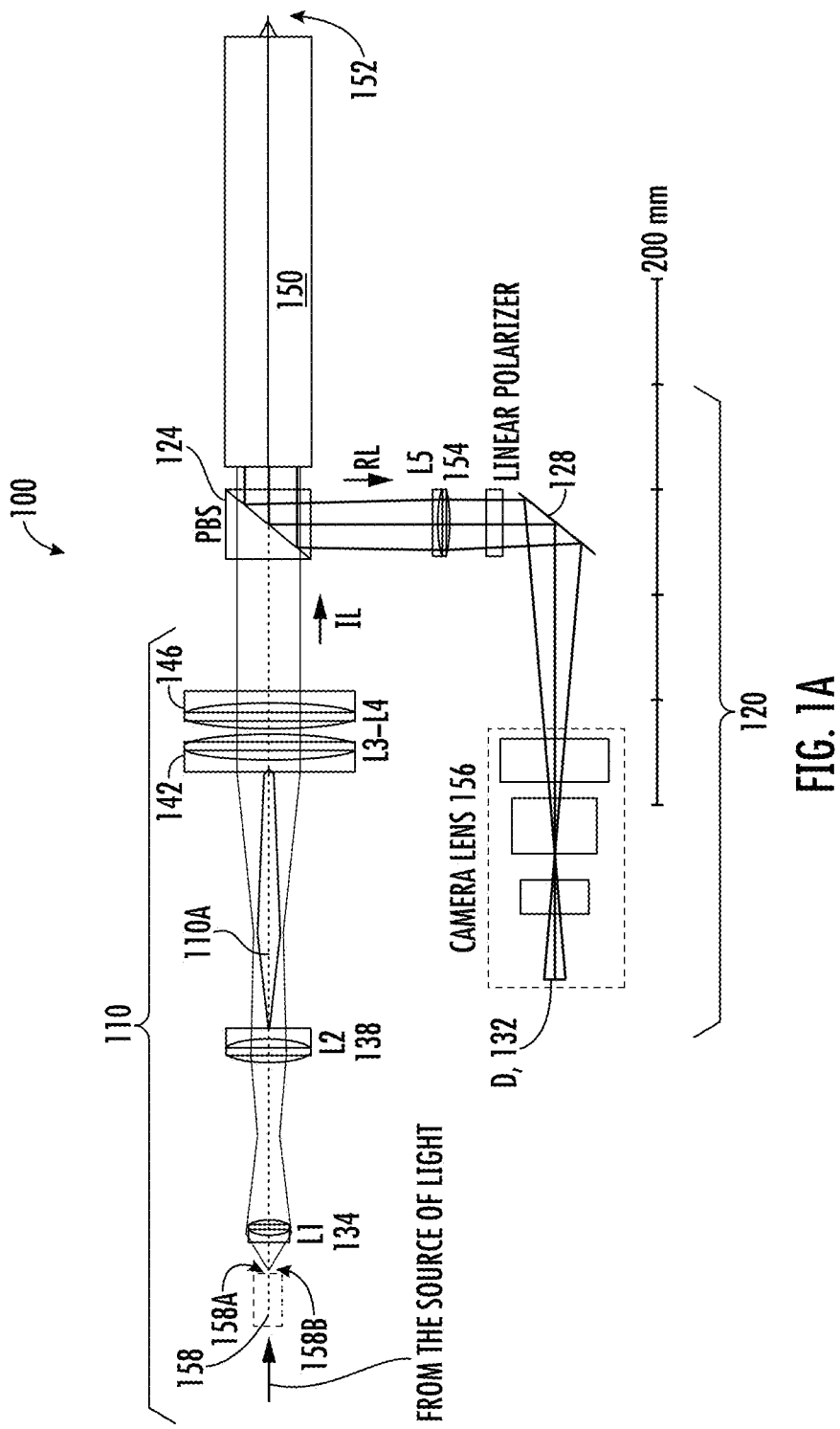
FIG. 1A is a schematic illustration of an embodiment of the LSCI fundus camera showing both the illumination and collection arms of the imaging system.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.

DETAILED DESCRIPTION

While implementations of the idea of the present invention were developed at least in part in response to a need to characterize anatomical and physiological dysfunction in the context of laser-induced branch retinal vein occlusion, and while the examples below are primarily addressing the use of such implementations in the context of characterization of biological tissues and, in particular, elements of an eye, it is understood that implementations of the discussed idea of the invention are generally and primarily directed to imaging of and determining characterizing various objects—be those inanimate objects or spaces (in particular, inanimate objects or spaces containing certain moving portions or elements) or living objects such as biological tissues hosting a flow of blood—all of these are within the scope of the invention. That said, the discussion of embodiments of the invention below is conducted with the specific examples of a target that is an eye, for simplicity and certainty of presentation only.

In particular, embodiments of the invention are configured to provide a specific non-contact and non-mechanically intrusive LSCI system judiciously configured to generate contrast-free and wide-field maps of blood flow with high spatial and temporal resolution—in a specific case, a retinal PSCI system. The proposed implementations of the LSCI method in vivo (in the context of laser-induced BRVO) was proven to be operable simultaneously characterize retinal anatomy and vascular morphology, quantify retinal hemodynamics, and assess features of cardiac and systemic vascular function (i.e., heart rate, vessel stiffness, peripheral resistance, contractility, and pulse propagation). Based on demonstrated results, it is believed that through further development, LSCI—that is currently not used for this purpose in related art—may become a robust imaging strategy for detecting early anatomical and physiological changes in retinal vascular diseases, neurodegenerative diseases such as Alzheimer's disease, and systemic cardiovascular diseases. Critically, this would enable early intervention prior to the onset of clinically detectable symptoms, improving disease management, identifying new prognostic indicators, and identifying novel biomarkers for assessing treatment efficacies in the clinical and pre-clinical settings.

The most commonly utilized clinical and pre-clinical retinal imaging modalities, such as OCT, OCT-A, and cSLO, have radically advanced the ability of a user to assess structural changes within the retina in response to injury or progression of a disease. As recognized in related art, however, these techniques are relatively insensitive to detecting alterations in vessel function(s) or hemodynamics, which limits the utility of these techniques as diagnostic tools in diseases with vascular etiology (such as diabetic retinopathy, for example) where dysfunction occurs years or even decades before the onset of anatomical abnormalities or the development of vision threatening symptoms. Importantly, the image-based clinical biomarkers identified with the use of these modalities have also yet to demonstrate strong correlations between anatomy and function. As has been recognized in related art (see, for example, Y. Li, X. Xia, & Y. M. Paulus, "Advances in retinal optical imaging," *Photonics* vol. 5, 2018), the current lack of ability to make desired predictions with these methodologies necessitates a shift in focus towards the development of techniques that can be used to make reproducible and quantitative measurements of physiological changes in the early, pre-symptomatic stages of retinal diseases.

Embodiments of the current invention address the opto-mechanical design of a custom LSCI instrument judiciously structured to produce high-speed (up to 590 fps), short-duration exposure (>50 µs) images of a predetermined target—in a specific case, a portion of a visual system (for example, the fundus) thereby allowing retinal hemodynamics to be measured with high spatial and temporal resolutions.

An embodiment of the proposed LSCI system, described below in reference to FIG. 1A, has several advantageous design considerations—at least in the context of characterization of a retinal surface.

Firstly, many commercial fundus cameras, especially those intended for use in small animals, are designed to be contact instruments (that is, employing either a front optical element that contacts the cornea directly, or the application of an applanating coverslip to adjust illumination and light collection through the pupil aperture). While contact instruments employed by related art are attractive due to their relatively simple optical design, the placement of any optical element on the corneal surface is likely to increase intraocular pressure and thereby alter ocular perfusion (especially in highly deformable vessels such as veins, for example). This consideration dictates that it is imperative that, contrary to the unwritten standards of the related art, the practically-successful system used for this purpose be capable of illuminating and imaging the fundus without any optical elements contacting the cornea.

Secondly, one of the major challenges of designing a non-contact instrument (which idea by itself introduces substantial complexity to the build and remains, therefore, non-obvious as related art clearly indicates) is achieving spatially-even illumination of the retinal surface without introducing glare from specular reflections off of the corneal surface and scattering off of the iris. Implementations of the idea of the invention (that is, embodiments of the LSCI system configured to measure changes in vessel function—including perfusion and flow velocity) successfully solve this problem. In overcoming this major challenge, which inevitably mars the performance of typical non-contact imaging systems of related art, an embodiment of the proposed LSCI instrument employs a combined use of polarization gating to block specular reflections from internal optics and the cornea and the principle of separation of pupil to illuminate the retina through that is imaged into the pupil plane. The former facilitates maintaining of the state of linear polarization of specular reflections and prevents the specularly-reflected light from entering the system's collection optics. The latter provides widefield, homogeneous illumination of the retinal FOV.

Thirdly, LSCI systems of related are limited in their ability to utilize the very same train of optical element to direct illuminating/irradiating light of variable or changeable degrees of coherence towards the object that is consequently imaged in backscattered light and, therefore, to operate for example in a regime of multiplexing two different types of light illuminating the object.

A skilled artisan having the benefit of this disclosure will readily understand that the persisting problem—manifesting in inability of the systems of related art, employed in the process of laser-speckle contrast imaging (LSCI) of the chosen object (whether inanimate or a biological tissue, such as retina) to form a substantially spatially even/uniform field of illumination of the object while, at the same time, avoiding glare caused by light that has been either specularly-reflected or scattered by portion(s) of the eye in front of the retina (as well as associated problems with achieving operationally-sufficient signal-to-noise ratio during such imaging process)—has been solved by configuring the LSCI imaging system according to an idea of the invention, that is as a combination of a judiciously-structured set of optical apertures (in one specific example only—the aperture(s) defined by or associated with an optical fiber component disposed to collect light from a chosen light source and to output this light from uniquely-dimensioned output end(s) of the optical fiber component) and an optical lens or group of optical lenses disposed to deliver such light from the set of apertures to the object. In one specific but not limiting case—with the use of this the following examples are presented—the object may be represented by an eye with its cornea and retina, and the discussed LSCI apparatus may be configured to investigate the characteristics of the retina, for example. Generally, the set of optical apertures is defined as one or more of distinct apertures limiting the spatial spread of light travelling therethrough. Here, when the set of optical apertures includes multiple optical apertures, at least some of these multiple optical apertures may be defined to be spatially separate and distinct from other apertures in the set. In one case, the set of optical apertures may be formed in an otherwise optically opaque screen separating the used source(s) of light from a group of optical lenses forming the trains of an optical illumination system of the discussed embodiments of the LSCI apparatus. In a related case, as implemented in the specific example discussed below, the set of optical apertures (through which light is delivered to the group of lenses relaying such light towards the object) can be defined by output end(s) of the optical fiber component which end(s) may contain multiple output end portions or areas that are located at different azimuthal angles with respect to an optical axis of the optical lens or group of lenses and at non-zero radial distances with respect to the optical axis as viewed in a plane transverse to such optical axis. In a very particular case, first and second of such output end portions or areas may be even diametrically opposed to one another with respect to the optical axis in such plane and/or that are not connected to one another with a material of the optical fiber component. In yet another related implementation, even when the optical fiber component is used to define the set of optical apertures, such set of optical apertures can be formatted to be optically conjugate to the output end(s) of the optical fiber component. As a result of implementation of these variations of the idea of the invention, the LSCI apparatus ma be configured such that substantially no light is received by the optical lens or group of optical lenses from the set of optical apertures at the optical axis, thereby leaving the axial portion of the front surface of the optical lens that faces the set of optical apertures (and, in a specific case, faces the optical fiber component defining such set) substantially not illuminated with light delivered to this front surface through the set of optical apertures from the employed source(s) of light.

Furthermore, according to the idea of the invention, the use of the set of optical apertures, delivering light towards the optical lens or a group of optical lenses that form a portion of an optical train of the illumination system of the discussed embodiments of the LSCI apparatus, allows to achieve a practical solution when different portions of input light—for example, first and second light having different degrees of coherence and/or different spectral bandwidths and/or differing from one another with respect to at least one additional optical parameter—are spatially-separated from one another at the input end of the illumination system of the LSCI apparatus. The advantage provided by such configuration manifests at least in the ability to have these different portions of input (object-illuminating) light be independently delivered through the optical train of the illumination system towards the object of interest, thereby providing flexibility of at least performing (i) the alignment the optical illumination system with respect to the object and (ii) the LSCI measurement of the object with the use of optical light-colleting system of the LSCI apparatus independently from one another, with respectively-corresponding portions of input light. Here, care is taken to practically avoid—in relevant cases—the situation when the light-sensitive object (for example, an object that may change its characteristics in response to being irradiated with particular light) is both pre-aligned and interrogated with the use of light having the same optical properties (in which case at the measurement step the already-affected and/or changed object—not the initial object of interest—is being characterized).

Therefore, generally, an embodiment of the LSCI imaging system is configured to form at the chosen target surface (which in operation of the system may be a surface of an inanimate object, or a biological tissue—for example, a corneal surface of an eye) such spatial distribution of illuminating light that does not cover the very central, axial portion of the cornea but rather includes area(s) separated— at the chosen target surface—by corresponding non-zero distance(s) from the axial portion. For example, the LSCI apparatus on one embodiment of the invention is structured to form a generally arcuately-shaped, around and separated from the chosen axis, distribution of illuminating light at the target surface. In a related specific case, the embodiment of the LSCI imaging system forms, in operation, a substantially ring-like spatial distribution of light at the target (for example—corneal) surface when illuminating such surface while leaving the axial portion of such surface not illuminated. As a corollary of such configuration, disclosed embodiments of the LSCI apparatus collects light returned from a portion of the object of interest through a portion of the target surface that is not covered by such distribution of illuminating light. (In the example when the apparatus is used for the purposes of imaging the retina of an eye, the apparatus may be configured to collect light returned from the retina through a portion of the cornea corresponding to a central, axial opening is such ring-like spatial distribution, that is, through the portion of the cornea that is not covered by such spatial distribution of illuminating light).

As used in this application and unless expressly defined otherwise, the terms "lenslet" and "lens element" are defined to refer to a single, simple, structurally-indivisible and employed singly stand-alone optical component that is bound—in an axial direction—by two optical surfaces and that changes the degree of convergence (or divergence, or collimation) of light passing through or traversing such component. In comparison, the terms "lens", "group of lenses", "lens system" and similar terms are defined to refer to a combination or grouping of lenslets or lens elements. The term "image" is defined as and generally refers to an ordered representation of detector output corresponding to spatial positions. For example, a visual image may be formed, in response to a pattern of light detected by an optical detector, on a display device such as a video screen or printer.

Further, for the purposes of description and claims, the term "optically-conjugate" and related terms are understood as being defined by the principal of optical reversibility (according to which light rays will travel along the originating path if the direction of propagation of light is reversed). Accordingly, these terms, as referring to two surfaces, are defined by two surfaces the points of which are imaged one on to another with a given optical system. If an object is moved to the point occupied by its image, then the moved object's new image will appear at the point where the object originated. The points that span optically-conjugate surfaces are referred to and defined as optically-conjugate points.

Specific Example of Embodiment of the LSCI System and Collection of Optical Data The schematic of the embodiment 100 of the LSCI imaging optical camera or apparatus is presented in FIG. 1A, in which the illumination arm (or optical illumination system denoted as 110) and the image-collecting arm (or optical light-collecting system labelled 120) are operably combined via a polarizing beam splitter (PBS) 124.

A part of the optical illumination art was defined by a judiciously structured optical fiber element (OFE) 158 of the apparatus 100, while the optical train that is shown in FIG. 1 to include lenses (L1, 134), (L2, 138), (L3, 142), and (L4, 146) formed another part of the same arm 110.

In FIG. 1A, the optical fiber component 158 is shown schematically with a dashed line, but its distal end portions 158A, 158B (giving, in operation, rise to a specifically spatially-structured light output from the component 158, as identified above) are expressly indicated. The custom-made optical fiber component (OFC, configured to transmit light from a source of light, not shown, towards the lens L1, 134) was structured to ensure that the object surface (in one case—a corneal surface) 152 was illuminated with a distribution of light the surface area of which is bound or defined by two curved lines. In one specific case, such spatial distribution of light was a ring-like distribution of light. In two different implementations, two implementations of the fiber optic component 158 were constructed. In one case, the component 158 was structured as a bundle including 39 micron wide core/0.33 NA borosilicate fibers, and the other case the element 158 was structured as a bundle including 39 micron wide core/0.28 NA borosilicate fibers. (Based on empirical results, the use of a 0.33 NA fiber was preferred, as it had lower insertion losses and higher throughput.) Each of the fiber-optic bundles was approximately 1 m long and otherwise the bundles were substantially identical with one another. The multiple distal ends shown as 158A, 158B in FIG. 1A of constituent optical fibers a given fiber-optic bundle were arranged at different azimuthal angles with respect to the optical axis 110A of the lenses 134, 136 (or, arm 110) as seen in a plane substantially perpendicular to the axis 110A. In a specific case, output aperture(s) at the output end/facet the OFC 158 were arranged in a ring with OD of about 2.13 mm and ID of about 1.34 mm, and a proximal end (that is, the end facing the source(s) of light) was dimensioned/shaped as a rectangle of about 2.0 mm in width by about 1.0 mm in height, to substantially match the elliptically-shaped cross section of the laser output beam to increase the efficiency of coupling of laser output light into the fiber bundle as discussed below.

Figure 9:
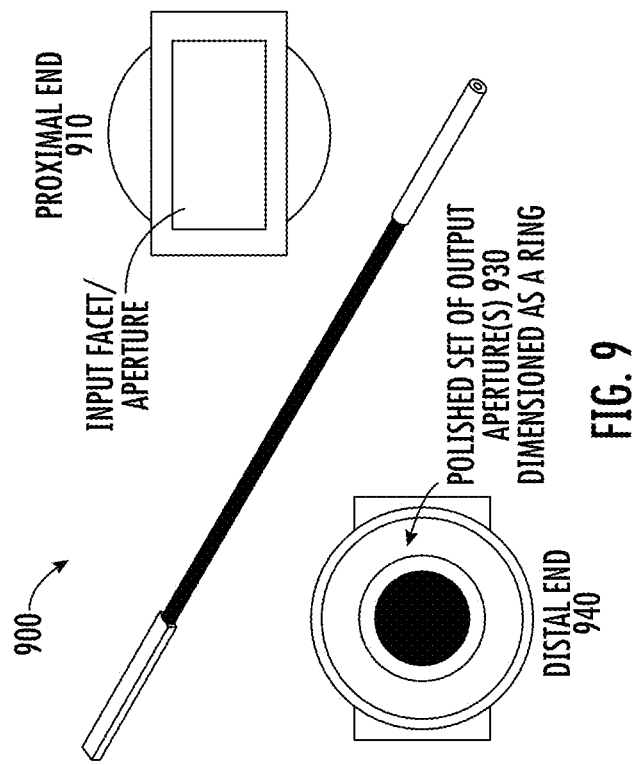
FIG. 9 illustrates a specific embodiment of a gadget defining a set of optical apertures 158. Here, such gadget is an optical fiber component, OFC, having specifically-dimensioned input (proximal) and output (distal) end facets. The fiber facet of the distal end defines the optical aperture(s) through which light, received by the OFC at its proximal end, is delivered towards the group of lenses of the optical illumination system of an embodiment of the PSCI apparatus.

FIG. 9 presents a schematic of a specific embodiment 900 of the OFC 158 that is configured have light output from a source of light be received at the proximal end 910, to transfer light through the OFC 900 towards the distal end 920 facing the lens 134 and to outcouple this light towards the lens 134 through the ring-shaped aperture 930 of the distal end 940 of the OFC 900. Specific numerical values, if depicted in FIG. 9, are but non-limiting examples of dimensions of the OFC 900.

In practice, a chosen source of light or, in some implementations—multiple sources of light, not shown in FIG. 1A—was/were separated from the lens L1, 134 by the optical element 158 different portions of the output optical aperture(s) if which are shown in FIG. 1 as 158A, 158B. (In other word, in reference to the embodiment 900 of FIG. 9, different generally non-overlapping with one another portions of the ring-shaped aperture 930 are represented in FIG. 1 as 158A, 158B). In a specific case, when it was necessary to deliver different light outputs, to the group of lenses L1-L4, through the set of optical apertures—for example, through the set of aperture(s) defined by the distal end of an embodiment of the fiber bundle OFC—and, in particular, when such different light outputs were characterized by different respectively-corresponding optical parameters (be such parameters optical wavelengths or degrees of coherence of light or polarizations), an embodiment of the LSCI system of the invention were configured to have multiple source of light coupled into the OFC via the optical fiber based splitter 1000, similar to that schematically shown in FIG. 10, in which multiple proximal ends 1000A, 1000B of the splitter 100 disposed to receive light from the respectively-corresponding multiple (two or more) sources of light 1010, 1020, etc. could be structured and/or dimensioned in a fashion similar to that of the end 910 of the OFC 900. In one specific case, for example, the OFC could be structured similarly to OFC 900 and have multiple (two or more, depending on the number of employed sources of light 1010, 1020, . . . ) proximal ends 1000A, 1000B each of which was coupled to the same distal end 940 via a fiber-based splitter. In this case, understandably, the embodiment of the LSCI apparatus is configured to have first light from the first source of light be acquired by the optical fiber component only through a first input facet, and second light from the second optical source be acquired by the optical fiber component only through the second input facet, while the optical fiber component itself is structured to substantially fully spatially overlap the first light and the second light upon propagation through the optical fiber component towards at least one output facet of the optical fiber component to substantially-completely illuminate such at least one output facet of the optical fiber component with either the first light or the second light or both the first and second lights.

Figure 10:
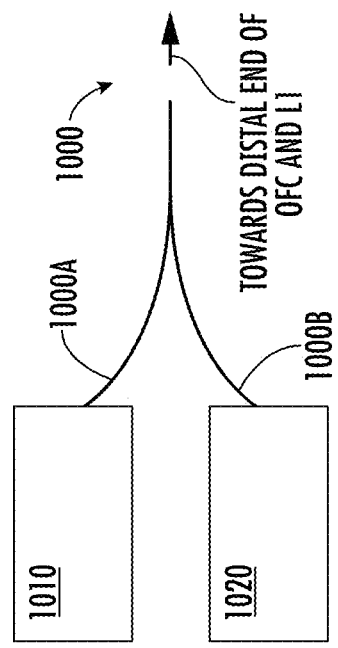
FIG. 10 is a schematic of optical coupling of light outputs from different sources of light to be delivered to the set of optical apertures separating the multiple sources of light from the group of lenses of the optical illumination system of an embodiment of the LSCI apparatus.

In one specific related example, however, the splitter 1000 may be structures such that a portion of the constituent optical fibers of the optical giber bundle is used to form one branch of the splitter (say, branch 1000A), while another portion of the constituent optical fibers is used to form another branch (in the example of FIG. 10—branch 1000B). When this is the case, the output facet of the OFC may be structured to include two (optionally—substantially concentric, stacked up one with another) ring-shaped apertures: one corresponding to and transmitting towards the lens L1, 134 light received at one branch of the splitter and another corresponding to and transmitting towards the lens L1, 134 light received at another branch of the splutter. In this latter case, understandably, the optical fiber component itself is structured to substantially fully spatially separate the first light and the second light upon propagation through the optical fiber component towards at least one output facet of the optical fiber component to substantially-completely illuminate only a first subset of such at least one output facet of the optical fiber component with the first light, and only a second subset of such at least one output facet of the optical fiber component with the second light (the first and second subsets of the at least one output facet of the optical fiber components being spatially distinct from one another).

In one example, a degree of coherence of light generated, in operation, by the source of light 1010 was lower than a degree of coherence of light generated by the source 1020 and, when these two sources were operated in a time-multiplexed fashion, light received by the lens 134 from the ring-shaped aperture 930 at the distal end 940 of the OFC were alternating pulses of light—one having a higher degree of coherence, the next having a lower degree of coherence.

Notably, the employment of the so-structured optical fiber component, according to the idea of the invention, also allowed for implementation of the Gullstrand's separation of pupil principle in the system 100. Here—when the system was used to characterize a visual system, and eye—reflexes from the cornea and iris of the eye the retina of which is being imaged are avoided by using separate areas of the pupil for illumination and collection. Specifically, in the case of the LSCI fundus camera 100, this principle was implemented with the use of illumination (of the corneal surface 152) that had a surface area bound by two curved lined while a portion RL of the illuminating light IL reflected by the retinal surface (behind the corneal surface 152; not shown) to form the image at the detector (D,132) through the optical light-collecting system is acquired through a portion of the corneal surface 152 that substantially does not overlap with such illuminated surface area limited by the two curved lines. (In a specific case, when the light distribution of illumination formed by the optical illumination system 110 at the object/corneal surface 152 is a ring-shaped distribution of light, light reflected from the retinal surface was collected substantially through the area that is central to (that is, through the center of) the ring-shaped distribution of illuminating light IL at the object surface 152. In one specific case, when the cornea of an eye was chosen as the surface 152—that is, at the corneal plane—the ring-like area of illumination had an internal diameter (ID) of about 0.8 mm and the outer diameter (OD) of about 1.5 mm. In this case, the return/reflected light was collected through the central, 0.7 mm diameter opening of (surface area "aperture" defined by) this ring.

In one case, the design of the illumination optics 134, 138, 142, 146 was performed with Zemax® optical design software. Light emerging from the distal ends 158A, 158B of the fiber optic component 158 was collected with the lens (L1, 134) and relayed via a relay telescope system (defined by the lenses 138, 142, 146) through a polarizing beam splitter 124, and into the back focal plane of an imaging bore 150 (in one example, such bore was a Bioptigen G4 mouse imaging bore, Leica Microsystems, Morrisville, NC). In practice, near-infrared achromatic lenses (available from Edmund Optics with technical parameters described, for example, at edmundoptics.com/p/12 mm-dia-x-15 mm-fl-nir-ii-coated-achromatic-lens/19998/, edmundoptics.com/p/25 mm-dia-x-45 mm-fl-nir-ii-coated-achromatic-lens/6250/, and edmundoptics.com/p/50 mm-dia-x-200 mm-fl-nir-ii-coated-achromatic-lens/7337/, which descriptions are incorporated herein by reference) were used in one embodiment of the system 100. The bore 150 was structured as an arrangement of lenses optimized for imaging the retina, and was designed to achieve a 40-degree FOV with 1.7 micron lateral resolution and is optimized and AR-coated for light at near infrared (NIR) wavelengths. The combined relay telescope and Bioptigen bore had a demagnification of about 1.675. With a 0.33 NA illumination fiber bundle, this resulted in about 50° visual angle (1.6 mm arc length) illuminated field of view, FOV, on the retinal surface through corneal surface 152, as modeled in Zemax using a murine eye model.

FIG. 1B presents a spot diagram representing the field of 785 nm light at the central portion of the corneal surface of the eye (that corresponds to the pupil of the eye) when the illumination is provided through only one chosen of the multiple output ends 158A, 158B. From the discussion provided above the skilled artisan will readily appreciate that, when the constituent ends of fibers of the OFC 158 are arranged in a ring, the complete illumination field would be an annulus—in one case, a substantially radially symmetric annulus, i.e. a complete spot diagram of the complete illumination field is obtained from that of FIG. 1B by rotating the spot diagram of FIG. 1B around its center.

FIG. 1C presents a spot diagram of light at 785 nm illuminating the retinal surface as produced by the embodiment 100 including the OFC 158 when the illumination is provided through only one chosen of the multiple output ends 158A, 158B. Each of the patterns of illumination produced by utilizing the remaining of the multiple ends of the OFE 158 substantially overlaps with the immediately-neighboring patterns, thereby substantially completely filling the 1.4 mm circle area at the retina and producing a substantially spatially-uniform illumination of the retina.

The probe's light-collecting optics 120 were also optimized in Zemax. The lens (L5,154) was placed behind the Bioptigen bore 150 such that the focal plane of the lens 154 was nominally at the back focal plane of the lens/bore 150. This combination makes the object surface 152 appear at infinity, thereby allowing for the surface 152 to be imaged with a camera lens 156 nominally focused at infinity. A 50 mm F/2.0 6MP manual focus Navitar camera lens (1-24424) was used in one experiment to focus the image of the cornea 152 onto a Basler Ace acA2040-180 km-NIR camera (a 2048×2048, 180 FPS, NIR camera) used as the detector 132. To allow for focus adjustment, the position of (L5,154) was then advanced such that the image appeared in the middle of the camera lens focus range (focal distance of 700 mm) instead of at infinity.

In the light collecting arm 120 of the system 100, the plane of the pupil of the eye (considered for simplicity to substantially coincide with the corneal surface) was optically conjugated to the aperture stop of the camera stop, and thus could be stopped down to reject reflections off of the cornea and scattering off of the iris, while still allowing collection of reflected light RL through an axial portion of the cornea (in one case—through the portion of the corneal surface corresponding to the center of the ring of the spatial distribution of illuminating light IL at the cornea).

Notably, according to the idea of the invention, the use of the PBS 124 (along with an additional "booster" polarizer 128 in the light-collecting arm 120, added in order to enhance the possibly low extinction ratio of the PBS 124) enabled the so-called polarization gating between the arms 110, 120 and ensured that only crossed-polarized light could be detected at the detector (D,132). As specular reflections maintain the state of polarization of incident light, but various birefringent and depolarizing structures present in the eye (and, in particular, the retinal nerve fiber layer, RNFL, and retinal pigment epithelium, RPE) rotate or scramble the polarization of light, the ability to detect only cross-polarized light at the optical detection arm 120 of the embodiment of the invention effectively filters out specular reflections from the cornea (as well as those formed at optics internal to the camera lens 156) and provides practical advantage over conventionally-used LSCI systems.

A person of ordinary skill in the art will now readily appreciate that, in designing of an illumination system or arm of a given LSCI system, the coherence of the source of light should be taken into account as it is critical to ensure optimal speckle contrast. In the present case, wherein the multimode light propagation through the fiber bundle can reduce spatial coherence—and, therefore, speckle contrast—a wavelength-stabilized laser source (Ondax Sure-Lock, Coherent Inc, Santa Clara CA) operating at about 785 nm with 50 MHz linewidth was chosen as a source of light. This corresponded to a linewidth of approximately 100 fm, or a coherence length of about 6 m, which was expected to easily exceed any modal dispersion in the fiber bundles while still providing sufficient coherence to maximize speckle contrast. The laser source of light had a maximum output power of 100 mW (measured before its integrated isolator) and an output beam with a substantially elliptical cross-section of about 0.9 mm-by-1.7 mm.

Another important consideration during the construction of the embodiment 100 of the LSCI apparatus was to maintain the ability to easily modify the opto-mechanical design to allow for imaging of multiple animal species (including humans) despite large variations in anatomy, axial length, pupil size, and refractive index of the target visual systems. In order to achieve this goal, both the illumination 110 and collection 120 arms of the LSCI system 100 were designed to be easily adjustable and constructed from existing commercial parts. As a consequence, the resulting design allows the user to substitute the front optical element (L1, 132) and adjust the illumination path to ensure the ring illumination is imaged into the subject's pupil plane, and thereby to apply the so-restructurable system 100 to multiple species, including humans in clinical applications.

Referring again to FIG. 1A, in one case of collecting optical data in light RL reflected from the retinal surface of an eye, the imaging camera 156 (complemented with the optical detector system 132) of the embodiment 100 included a high frame rate camera (up to 590 fps at 500×500 pixel squared area), utilized tunable laser power, and employed exposure control ranging from about 50 μs to about 10 s. Firstly, a high frame rate camera facilitated the maximizing of temporal resolution and ensured adequate sampling of the optical field (which may be rather important in some cases, for example considering that the normal mouse heart rates ranges from 500 about beat per minute, bpm, to about 700 bpm in the awake state). Secondly, imaging sensitivity to object space elements moving at high speeds is considered to be higher at shorter exposure times while sensitivity to a slow motion improves with increasing exposure times, and the linearity between relative changes in speckle contrast-based estimates of a flow rate and absolute speed of particles forming such a flow is known to improve when exposures are taken across a range of values. Accordingly, the embodiment of the invention was structured to be capable of capturing images over a range of exposure durations, with a wide range of exposure control to not only for image high and low flow regions of the object space with maximum sensitivity, but potentially to enable absolute quantification of flow rates through a multi-exposure LSCI strategy.

In advantageous contradistinction with related art, employing modulation of intensity of illumination of a target by pulsing light output from the laser source with the use of an acousto-optic modulator (AOM), the illumination intensity employed in the current embodiment was made inherently substantially laterally homogenous due to the use of a multimode fiber bundle and its resulting top-hat output intensity profile. Furthermore, the illumination field was equalized independently from the exposure time by controlling laser power and digital light sensitivity through gain manipulation.

Considerations for Practical Implementation of Imaging With the Use of an Embodiment of the Invention To demonstrate the use of the embodiment of the system in practice, BRVO was performed in age-matched male and female C57BL/6J mice. Age-matched male and female C57BL/6J mice (The Jackson Laboratory, Bar Harbor, Maine) were housed in the Biomedical Resource Center at the Medical College of Wisconsin (MCW) under a 12:12 light-dark cycle with food and water ad libitum. All animal protocols were reviewed and approved by the Medical College of Wisconsin Institutional Animal Care and Use Committee and conform with National Institute of Health (NIH) and Association for Research in Vision and Ophthalmology (ARVO) guidelines for the Care and Use of Laboratory Animals.

Eye pupils were dilated using a combination of 2.5% phenylephrine (Paragon BioTeck, Portland, OR) and 1% tropicamide (Akorn, Lake Forest, IL), mice were sedated following intraperitoneal administration of injectable anesthetic (10 mg/kg xylazine 60 mg/kg ketamine solution), and moisture of the eyes was maintained using Systane Ultra lubricant eye drops (Alcon Inc., Fort Worth, TX). Vein occlusion was induced by photocoagulation with a green laser diode. Retinal veins were irradiated with a 532 nm diode laser (Index, Mountain View, CA) with the following parameters: 100 micron spot size, 200 mW laser power, 0.4 sec exposure duration, and 4 spots per vein. A 5.4 mm fundus contact lens (Ocular Instruments, Bellevue, WA) was used to focus laser light onto the retinal vessel until a white endpoint with vascular narrowing was achieved. Mice were recovered from anesthesia with 5 mg/kg atipamezole.

To ensure that thermal injury to the retina was avoided, laser power levels were kept below the Group 1 limits defined by ophthalmic and lens standards such as, for example, ANSI z80.36:2016. For the used 785-nm light source and a retinal FOV of 50 degrees (producing about 1.6 mm of arc length on mouse retina, as modeled in Zemax), this limit was computed to be 22. 1 mW, restricted by the "Retinal infrared radiation thermal hazard" defined in the standards. Images were nominally acquired with at most 8.35 mW incident on the mouse cornea, as measured with a calibrated power meter (Newport Power Meter, Model 1931-C, Irvine, CA).

In vivo retinal LSCI with the use of the embodiment 100 and with the confocal scanning laser ophthalmoscope (cSLO—Heidelberg Engineering) were both performed under inhaled anesthesia. Anesthesia was induced using 5% isoflurane in 100% oxygen before being reduced to 2% isoflurane for maintenance. Pupils were dilated using a combination of 2.5% phenylephrine (Paragon BioTeck, Portland, OR) and 1% tropicamide (Akorn, Lake Forest, IL). Moisture of the eye was maintained during imaging with the use of Systane Ultra lubricant eye drops (Alcon Inc., Fort Worth, TX). Mice were stabilized on an imaging stage with the capability for 2 degrees of rotation and 3 degrees of translation. Fluorescein angiography (FA) was performed 30 seconds following subcutaneous administration of 0.5 mg fluorescein (10% AK-Fluor, Akron Pharmaceuticals, Lake Forest, IL).

The operation of image processing (following the collection of data with the embodiment of the LSCI apparatus disclosed above) was performed as discussed by D. D. Patel and D. M. Lipinski in *Sci. Rep.* 10, 7177 (2020) on MATLAB using a custom script to read raw speckle images, generate speckle contrast maps via either temporal processing (for high spatial/low temporal resolution contrast maps) or spatial processing (for high temporal/low spatial resolution contrast maps), and with the use of Fourier analysis in order to segment retinal arteries from veins and to map time delay in pulse wave propagation.

Retinal Imaging With the Use of an Embodiment of LSCI Apparatus

Assessing the Effect of Mean Pixel Intensity on Mean Speckle Contrast

During LSC-imaging, experimental noise such as variance in mean pixel intensity resulting from changing exposure durations, laser power, or digitally amplifying light sensitivity of the camera's charged-coupled device (CCD) sensor by adjusting gain may affect speckle contrast measurements. Hence, it is important to understand the effects of exposure time, laser power, and gain on mean pixel intensity of raw speckle images and consequently speckle contrast measurements.

In the embodiment 100 of the imaging apparatus, the exposure time and gain can be set through the image acquisition software, while laser power output can be controlled by adjusting the drive current applied to the laser diode, where current (mA) and laser power (mW) have a linear relationship (FIG. 2A). To understand the effect of mean pixel intensity of raw speckle images on measured speckle contrast, a rigid surface was positioned orthogonally 2 cm from the front optical element of the imaging bore and LSCI was performed at 3 ms exposure duration while varying drive current (35-150 mA) and gain (0.27-24.08 dB) (FIG. 2B). LSCI under varying gain and drive current settings was repeated at 1 ms and 5 ms exposure durations. For each of the 390 combinations of imaging parameters evaluated, the mean speckle contrast was measured across 25 temporally processed frames (N=12 sets) and plotted against the mean pixel intensity (0-255 AU) measured across the corresponding raw speckle images (FIG. 2C). Regardless of exposure time (1, 3 or 5 ms), the relationship between mean speckle contrast and mean pixel intensity was observed to be linear between 15 and 135 AU, but variance increased significantly beyond those thresholds (FIG. 2C). Importantly, this demonstrates that measurements of mean speckle contrast are not overly sensitive to either exposure time or pixel intensity, except under extremely dim or saturating conditions.

Accordingly, results presented in FIGS. 2A through 2C demonstrate that regardless of exposure time, mean speckle contrast appears to be minimally—if at all—affected by change in mean pixel intensity between 15-135 AU, while variance in speckle contrast measurements is noticeably increased under very dim (mean pixel intensity <15 AU) or saturating illumination conditions (>135 AU).

Investigation of the sensitivity of speckle contrast measurements to changes in laser power or gain at any fixed mean pixel intensity between 15 and 135 AU was further performed. For 11 different combinations of drive current and gain settings at 1 ms exposure and 9 different combinations at 5 ms, we demonstrate the ability to achieve a target mean pixel intensity of 100 AU with minimal variance (±0.34 AU at 1 ms; ±0.30 AU at 5 ms) (FIG. 3A). Plotting the variance from the mean speckle contrast measured across all conditions (FIGS. 3B, 3C) against laser power and performing a simple linear regression analysis revealed a weak negative correlation between variance from mean speckle contrast and laser power at 1 ms and exposure durations ($R^2$=0.2739 and $R^2$=0.034, respectively), suggesting that variance from mean speckle contrast may increase under low power/high gain conditions.

Understanding the effect of exposure duration, laser power, and gain on mean pixel intensity of raw speckle images helps to establish imaging guidelines for improving accuracy of speckle contrast measurements. For best imaging practices, we demonstrate that it is essential to maintain a mean pixel intensity of raw speckle images between 15-135 AU while maximizing laser power over gain to ensure adequate sampling and minimize variance in speckle contrast measurements.

In other words, it was practically demonstrated that any fixed mean pixel intensity can be achieved through multiple combinations of gain and laser power settings. Having established that the working range of raw pixel intensity for our LSCI sessions should be between 15-135 AU, the sensitivity of speckle contrast measurements to gain and power manipulation at any fixed mean pixel intensity within this range was established. It was demonstrated that variance from mean speckle contrast has a weak negative correlation with increasing laser power and consequently decreasing gain (with such trend being more prominent under shorter exposure duration settings, suggesting that for best imaging practices maximizing laser power should be prioritized over increasing gain to avoid under-sampling and increased variance in speckle contrast measurements.

Repeatability of Speckle Contrast Measurements In Vivo

Having gained appreciation of the effects of laser power, exposure, and gain on the generation of laser speckle contrast images and having established the ability of our custom system to reproducibly image a static surface under a wide array of conditions, the repeatability of in vivo LSCI measurements in the murine retina was further explored. Specifically, as the positioning of experimental animals relative to the LSCI imaging bore 150—with respect to both distance and angle—was found to be important to achieving uniform illumination of the retinal surface, a repeatability study was performed in which raw speckle images (N=100 frames/session) were obtained (170 fps, 5 ms exposure, and 120 mA) over three separate imaging sessions, between each of which positioning of the animal, contact lens (used to prevent corneal desiccation), and X, Y, Z positions of the imaging stage relative to the bore were reset. Following spatial processing, the average speckle contrast was measured at multiple vessel locations (V1-V5) across the retina for each session (the results are shown in FIGS. 4A, 4B, 4C) and an intra-rater reliability study was performed. Using a 2-way mixed effects model, an intraclass correlation coefficient (ICC) of 0.946 (CI: 0.762-0.994) was demonstrated (see FIG. 4E), with no statistically significant variance between speckle contrast measurements observed at any vessel location between sessions, indicating a high degree of repeatability.

The following portion of the discussion is presented in reference to the section on Description of Some Empirical Results (below). After determining the optimal imaging practices, in vivo retinal LSCI was performed in the pathological setting of BRVO to demonstrate the ability of LSCI to assess retinal vascular anatomy and function. Using a Fourier analysis approach similar to that described by Postnov et al. (2018), we first separate retinal veins from arteries on speckle contrast maps (illustrated in FIGS. 5A, 5B, 5D, 5E). Upon following each mouse over 14 days, we noted several advantages and disadvantages of LSCI over near-infrared imaging (NIR) and fluorescein angiography (FA) for monitoring disease progression. Notably, on Day 1 post-treatment, retinal vein stenosis and occlusion is evident on LSCI, but difficult to detect on NIR due to the presence of a hyperreflective lesion at the burn site. On FA, vessel damage and leakage also result in hyper-fluorescence which makes it difficult to detect anatomical alterations (see FIGS. 5C, 5F). By Day 3, we observed increased patency of the retinal veins and reperfusion on LSCI and FA which was not evident on NIR imaging. At this time, one of the obvious disadvantages of LSCI relative to FA is apparent—the inadequate resolution of secondary and tertiary retinal blood vessels. Areas of hypo-perfusion in smaller vessels at the site of treatment is evident on FA by Day 3, but difficult to visualize on LSCI. Nevertheless, while FA simply allows us to visualize the presence of fluorescein dye, speckle contrast maps allow us to quantify relative flow and perfusion across the entire field-of-view, allowing us to visualize and quantify relative perfusion outside of primary vessels. Using a speckle contrast colormap, we can detect the areas of hypoperfusion (areas with increased speckle contrast) that correlate with areas of hypoperfusion on FA (see FIG. 5G). By Day 14, we observe increased vessel tortuosity, vessel dilation, vessel thickening, and tissue contracture following retinal injury (FIGS. 5C, 5F). While retinal injury and hypopigmentation is more apparent on NIR, vascular morphology and flow is better visualized and quantified via LSCI and FA. However, in FA, an injured vessel may leak fluorescein and obscure fine adjacent detail, making it difficult to observe any secondary or tertiary vessels. Overall, LSCI enables contrast-free characterization of vascular morphology despite the presence of significant retinal damage, hemorrhaging or edema. Unlike FA, LSCI also enables quantification of relative flow across the entire field-of-view.

The ability of embodiments of the LSCI apparatus of the invention to quantify relative flow across several retinal vessels before and over the course of BRVO and to accurately delineate arteries from veins was further demonstrate (FIGS. 6A, 6B, 6C, 6D). Importantly, it was observed that mean blood flow through a reference vessel (RV) located outside of the laser treatment site was only modestly affected over time and variance was more likely due to changes in total blood flow to the retina than laser-induced damage (FIGS. 6E, 6H). By contrast, mean flow rates were noticeably reduced in the irradiated vein (V) and artery (A) on Day 1 post laser treatment, with lesser effect on the artery than vein—likely due to the less compliant and more muscular arterial walls which can withstand laser-induced damage and compression from localized edema (FIGS. 6E, 6H). The mean flow rates begin to recover in the irradiated vessels by Day 3, with quicker recovery seen in the artery over vein (FIGS. 6F-6H). However, by Day 14 we observe an overall reduction in mean blood flow rate across all retinal vessels, likely due to increased resistance to flow following compression of retinal vessels following the significant retinal atrophy and tissue contracture evident on the speckle contrast map (FIG. 6D). These changes in blood flow rate are difficult to appreciate on NIR or FA, making the ability of LSCI methodology performed with the use of an embodiment of the invention to characterize and especially quantify structural changes in retinal vascular anatomy and retinal hemodynamics—with high temporal resolution and over a wide field-of-view—a powerful tool for studying disease progression and monitoring treatment efficacies, in advantageous contradistinction with LSC-imaging performed with the use of the systems of related art.

Besides monitoring the vascular changes implicated in DR, AMD, and glaucoma, another promising application of discussed embodiments of the LSCI apparatus may be in the early detection of Alzheimer's disease and mild cognitive impairment—both of which have been associated with narrowing of retinal veins and decreased retinal venous blood flow in humans.

The ability to reliably perform LSCI at high frame rates by modulating exposure duration and laser power to ensure mean pixel intensity falls in the linear range (15-135 AU) enables the quantification of several parameters of systemic vascular and cardiac health (i.e. heart rate, pulse wave propagation, cardiac contractility, vessel stiffness, and peripheral resistance) which are difficult and laborious to achieve with other advanced ocular imaging modalities.

While several of these parameters can measured using other techniques, including pulse-oximetry or non-tethered electrocardiogram, results of the present experimentation proved that LSCI uniquely allowed for the simultaneous monitoring of blood flow and pulse wave velocity across multiple vessels within a single field-of-view (FIGS. 7B, 7C). Doing so allowed for comparison of blood flow waveforms between retinal arteries and veins to subsequently measure delays in pulse wave propagation between the retinal arterial and venous circulation (FIGS. 7E, 7F, 7G, 7H). Upon comparing blood flow between a retinal artery and retinal vein, we observe in increase in pulse wave propagation time from 11.68 ms under 2% isoflurane to 32.11 ms under 5% isoflurane (FIGS. 7G, 7H). These data are consistent with those of related art that demonstrated that the temporal variations in the sinusoidal venous flow waveform, upstream of the right atrium, results not only from the forward propagating pulse pressure wave following systole, but also from the backwards propagating pressure wave from right atrial filling during late diastole. Hence, it is feasible to use LSCI-based blood flow waveforms and wave propagation delay to better understand right atrial filling pressures, cardiac contractility, and venous return. In the current case, the increased time delay between arterial and venous flow waveforms at 5% isoflurane may have resulted from an overall decrease in venous return and delayed atrial filling—resulting from the combination of severe high-dose isoflurane-induced hypotension due to decreased peripheral vascular resistance and impaired cardiac contractility.

Figure 8A:
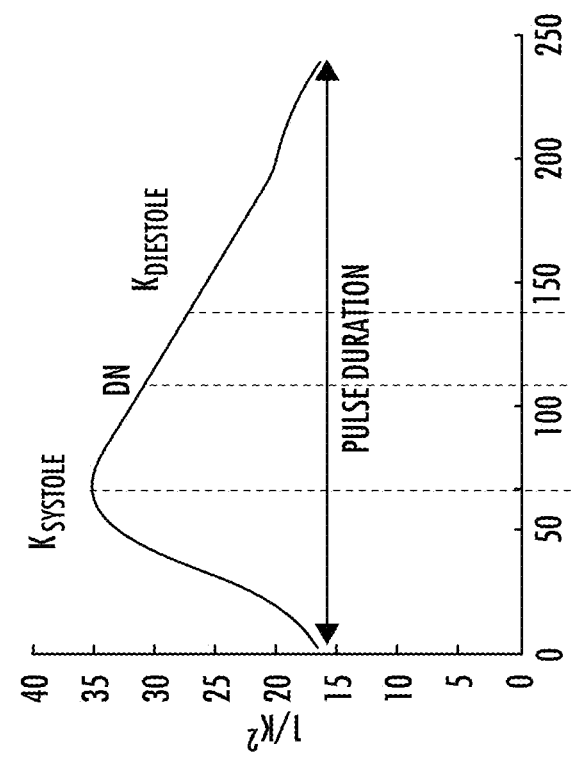
FIGS. 8A, 8B, 8C, and 8D: Pulse Wave Analysis using LSCI. Variation in speckle contrast with cardiac pulsatility results in a waveform that is proportional to pulse waveforms observed on photoplethysmogram. The average of five arterial LSCI-based pulse waveforms measured within the same ROI (shown in FIGS. 7B, 7C) under 2% isoflurane and 5% isoflurane are shown in FIGS. 8A, 7B. Here, $K_{systole}$ is the relative speckle contrast-derived flow rate at the peak of systole, $K_{diastole}$ is the relative speckle contrast-derived flow rate at the peak of diastole, DN is the dicrotic notch, $\Delta T$ is the time between $K_{systole}$ and $K_{diastole}$, and CT is the crest time, or the time from the start of the waveform to $K_{systole}$. The $2^{nd}$ derivative of each averaged waveform is shown in FIGS. 8C, 8D. Here, $K_a$ is the early systolic positive wave, $K_b$ is the early systolic negative wave, $K_e$ is the early diastolic positive wave.
Figure 8B:
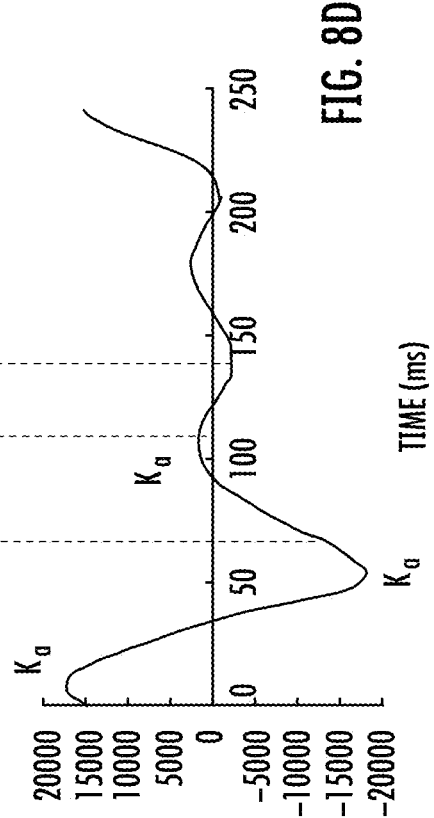
Figure 8C:
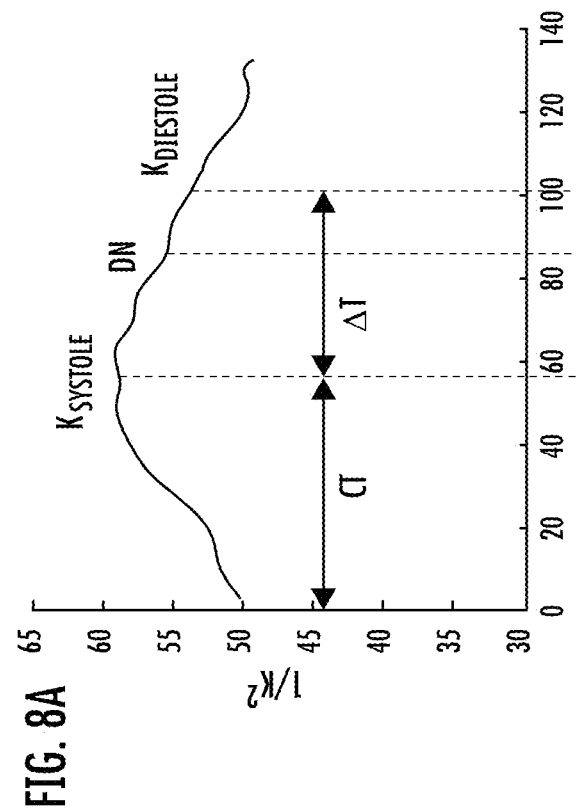
Figure 8D:
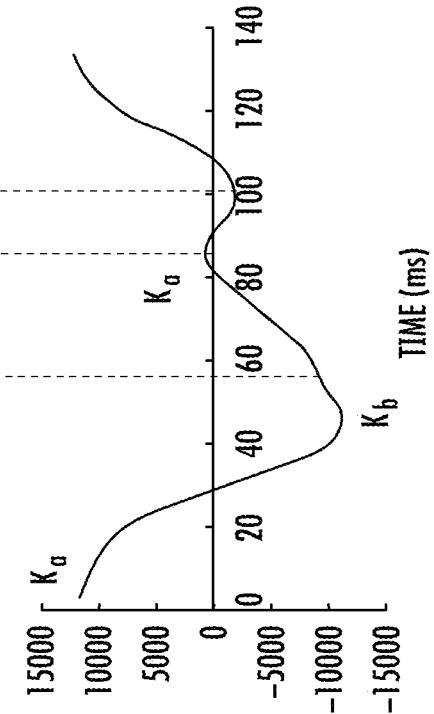

The blood flow waveforms measured by LSCI were also well correlated with pulse waveforms detected by photoplethysmography (PPG) in related art. Hence, LSCI-based pulse waveforms may be used to extract meaningful parameters of cardiac and systemic vascular function. In FIGS. 8A through 8D, the average of 5 arterial waveforms under 2% isoflurane and the average of 5 arterial waveforms under 5% isoflurane are demonstrate (FIGS. 8A, 8C). Also shown to highlight inflection points in each waveform are the $2^{nd}$ derivatives of each signal (FIGS. 8B, 8D). Based on the characterization of fingertip PPG by Elgendi (discussed in *Curr. Cardiol. Rev.* 8, 14-25, 2012), it was possible to label critical parameters on the speckle contrast-based flow waveforms (FIGS. 8A through 8D). Here, the $K_a$ wave in the $2^{nd}$ derivative represents the early systolic positive wave, $K_b$ wave represents the early systolic negative wave, $K_e$ represents the dicrotic notch (DN) or the closure of the aortic valve, $K_{systole}$ represents the relative speckle contrast-based flow rate at the systolic peak, $K_{diastole}$ represents the relative speckle contrast-based flow rate at the diastolic peak, crest time (CT) is the time from the start of the waveform to $K_{systole}$, and $\Delta T$ is the time between $K_{systole}$ and $K_{diastole}$.

Table 1 summarizes several parameters measured under 2% and 5% isoflurane. Firstly, a significant decrease in blood flow rate was observed under 5% isoflurane at peak systole ($K_{systole}$) and peak diastole ($K_{diastole}$) (Table 1). Previous studies had suggested that high-dose isoflurane results in severe hypotension from a decrease in peripheral vascular resistance. In applying Ohm's law to hemodynamics, one could note that blood flow should increase with an overall decrease in resistance to flow. However, severe hypotension may also lead to impairments in coronary autoregulation and consequently, impaired myocardial contractility. Hence, a decrease in resistance to flow from peripheral vasodilation and a decrease in blood pressure due to decreased peripheral vascular resistance, decreased heart rate, and decreased contractility (resulting in overall decrease in cardiac output), support the decrease in $K_{systole}$ and $K_{diastole}$ observed under 5% isoflurane.

TABLE 1

Summary of murine cardiac parameters measured from LSCI-based retinal arterial pulse waveforms under 2% and 5% isoflurane (N = 5). Significance was determined by two-tailed Student t-test.

| Parameter | 2% Isoflurane | 5% Isoflurane | p-value |
|---|---|---|---|
| Systolic peak amplitude ($K_{systole}$) | 59.79 ± 1.62 | 35.57 ± 1.01 | <0.0001 |
| Crest time (CT), ms | 55.29 ± 7.38 | 66.45 ± 3.26 | 0.0547 |
| Diastolic peak amplitude ($K_{diastole}$) | 54.29 ± 1.32 | 27.56 ± 1.99 | <0.0001 |
| Time to diastolic peak, ms | 99.95 ± 3.57 | 141.95 ± 12.69 | 0.0029 |
| Time to dicrotic notch (DN), ms | 85.59 ± 4.76 | 111.64 ± 12.47 | 0.0191 |
| $K_b/K_a$ ratio | −1.01 ± 0.09 | −1.05 ± 0.11 | 0.5628 |
| IPA ratio ($A_2/A_1$) | 0.56 ± 0.07 | 0.93 ± 0.20 | 0.0269 |
| Pulse duration, ms | 133.97 ± 1.46 | 235.51 ± 3.03 | <0.0001 |
| ΔT, ms | 44.66 ± 8.06 | 75.49 ± 12.83 | 0.0098 |
| Augmentation Index ($K_{systole} - K_{diastole})/K_{systole}$ | 0.55 ± 0.10 | 0.42 ± 0.10 | 0.0890 |

Beyond anesthesia, $K_{systole}$ and $K_{diastole}$ may also be affected by sympathetic or parasympathetic activation, administration of pharmacologic vasoconstrictors and vasodilators, and hypovolemia—broadening the application of this retinal LSCI system towards assessing systemic physiological changes in response to fluid status, nervous system function, and pharmacologic treatments.

Also noted in Table 1 is a significant increase in the inflection point area (IPA) ratio ($A_2/A_1$), where $A_1$ is the area under the waveform from the start of the pulse wave to the DN, and $A_2$ is the area under the waveform from DN to the end of the pulse wave (Table 1). The IPA ratio is inversely proportional to the total peripheral resistance. In current experimentation it was found that 5% isoflurane significantly increased IPA ratio, therefore supporting previous findings that high-dose isoflurane reduces peripheral vascular resistance. Related art also suggested that pulse wave reflection is influenced by the impedance mismatch between the compliance of large elastic arteries and peripheral resistance, which is predominantly regulated by small arterioles. Hence, reduced peripheral resistance or increased large vessel compliance would both contribute to a delay in pulse wave reflection and therefore prolonged ΔT, or the time it takes for a pulse pressure wave to travel from the heart to the periphery and back. As expected, ΔT was increased significantly under 5% isoflurane (Table 1).

However, whether ΔT prolongation was due to decreased peripheral resistance or increased compliance of large elastic vessels requires further investigation. CT, $K_b/K_a$, and the augmentation index ($K_{systole}-K_{diastole})/K_{systole}$) are features of PPG analysis that are associated with arterial stiffness, large vessel compliance, and often used to classify risk of cardiovascular disease such as atherosclerosis [44,47-50]. Here we found no significant difference in CT, $K_b/K_a$, and augmentation index under 2% isoflurane and 5% isoflurane, suggesting that the effect of high-dose isoflurane may primarily be on peripheral vascular resistance with lesser effect on large vessel compliance (Table 1).

The ability of the proposed embodiment of the LSCI system to measure peripheral vascular resistance and large vessel compliance through non-invasive assessments of retinal blood flow makes it a powerful tool for also studying vascular aging and hypertension (correlated with IPA ratio) or monitoring risk of more serious cardiovascular conditions such as peripheral, carotid, or coronary artery occlusion (correlated with augmentation index) or athero- and arteriosclerosis (correlated with $K_b/K_a$ ratio, CT, and ΔT).

Furthermore, under 5% isoflurane, significant increases in pulse duration were observed (Table 1). The increase in pulse duration under 5% isoflurane correlates with the observed decrease in heart rate (FIG. 7D). However, the reduced heart rate in conjunction with reduced stroke volume—as suggested by the significantly reduced flow rate at peak systole ($K_{systole}$)—further supports the argument that high-dose isoflurane impairs regulation of cardiac output, likely due to simultaneous isoflurane-induced hypotension and suppression of myocardial contractility.

Lastly, volatile anesthetics like isoflurane have shown left ventricular dysfunction by delaying left ventricular isovolumetric relaxation and consequently impairing left ventricular filling. Diastole begins upon closure of the aortic valve and isovolumetric relaxation of the left ventricle. Consequently, delayed isovolumetric relaxation would prolong time to the DN (the closure of the aortic valve) and prolong time to peak diastole ($K_{diastole}$)—both of which were observed under high-dose isoflurane (Table 1).

Discussion of Some Empirical Results

(A) Branch Retinal Vein Occlusion

In order to assess the ability of LSCI to detect pathologic changes in vessel structure and function compared to traditional imaging modalities, we imaged the murine retina (N=5 eyes) with LSCI, fluorescein angiography (FA), and near infrared (NIR) imaging with a confocal scanning laser ophthalmoscope (cSLO) before and then 1, 3, and 14 days after inflicting laser-induced BRVO. Healthy retinae in all eyes were observed to have normal vascular structure before BRVO (FIGS. 5A, 5D) and arteries and veins could be accurately segmented by Fourier analysis using a technique described in detail by Postnov et al. in *Biomed opt express.* 9(12):6388-6397 (2018), see FIGS. 5B, 5E.

NIR imaging, 1-day post-laser treatment, reveals focal lesions with a hyperreflective center and pale outer ring suggestive of retinal thermal injury in all eyes (FIGS. 5C, 5F). FA revealed hyper-fluorescence at the site of laser treatment and in the microenvironment surrounding the affected retinal vessels—indicative of vessel damage FIGS. 5C, 5F). FA in Mouse ID 2 at Day 1 also reveals non-perfusion to some arterioles, venules, and capillaries at the site of laser injury (FIG. 5F). LSCI in Mouse ID1, 1-day post-laser treatment, demonstrated stenosis in a retinal vein (FIG. 5C, yellow arrow) and vein occlusion (FIG. 5C, red arrow), with little to no effect on retinal arteries within the burn site. Likewise, LSCI in Mouse ID2 revealed stenosis (FIG. 5F, blue arrow), 1-day post-laser treatment. On Day 3 post-laser treatment, NIR imaging showed hyper-reflectivity at the lesion in both mice, but notably reduced hyper-fluorescence and leakage as confirmed by FA. While FA and LSCI demonstrate reperfusion and increasing patency of the primary retinal veins at Day 3, FA, especially in Mouse ID2, reveals areas of hypo-perfusion in smaller retinal vessels of the deeper plexi. These areas of hypo-perfusion can be observed upon LSCI, where areas of increased speckle contrast correspond to areas with reduced blood flow (FIG. 5G). By Day 14, retinal injury and hypo-pigmentation is evident on NIR, however blood flow in major retinal arteries and veins appears unaffected on FA and LSCI. Nevertheless, as highlighted on FA and LSCI, retinal injury with likely secondary scarring and atrophy has forced tissue contracture and adduction of retinal vessels towards the affected primary vein in both mice (FIGS. 5C, 5F). Venous dilation (white arrow) and increased tortuosity (green arrow) is also apparent in Mouse ID2.

In order to quantify pathological changes in retinal hemodynamics over the course of disease, speckle contrast derived blood flow rates ($1/K^2$) were also assessed across a reference vessel (RV), outside of the laser treatment site, as well as a retinal vein (V) and retinal artery (A), within the treatment site, prior to laser-induced BRVO, and then 1, 3, and 14 days following laser treatment (FIGS. 6A through 6G). Analysis of mean blood flow rates across these retinal vessels demonstrates that—relative to blood flow rates measured prior to laser-inflicted BRVO—mean flow rate is modestly reduced in RV (−10%) on Day 1 post-treatment, whereas mean flow rate is more drastically reduced in V (−83%) and A (−40%) (FIG. 6H). Also noticeable on flow profiles is a reduction in the vessel diameter of V on Day 1 post-treatment (FIG. 6F). Vessel diameters and blood flow rates begin to recover across V (−33%), and A (−0%) by Day 3, however, by Day 14 we observed an overall reduction in blood flow rates across all retinal vessels relative to pre-treatment levels: RV (−16%), V (−40%), and A (−15%) (FIGS. 6E-6H). These results show that the most significant impact of laser treatment for BRVO is on retinal vessels directly within the irradiated area. More specifically, the effect of laser treatment on mean blood flow rate is more prominent on veins than arteries, with the latter demonstrating a quicker recovery over time (FIG. 6H).

(B) Evaluating Cardiac Function with LSCI

A murine retina was imaged at 376.2 fps at 2.5 ms exposure duration, after which Fourier analysis was applied to classify retinal arteries from retinal veins (FIG. 7A). The mouse was imaged under 2% isoflurane (FIG. 7B) and 5% isoflurane (FIG. 7C). Fourier analysis on a 2.66 s recording (1000 frames) identified the first harmonic frequency at 4.51 Hz under 5% isoflurane and 7.52 Hz under 2% isoflurane, representing heart rates of 270.6 bpm and 451.2 bpm, respectively (FIG. 7D). Average speckle contrast from an artery and vein under 2% isoflurane (FIG. 7E) and 5% isoflurane (FIG. 7F) were plotted against time after applying a moving average filter of 15 data points. Fourier analysis reveals an average pulse wave propagation time delay of 11.68 ms under 2% isoflurane (FIG. 7G) and an average pulse wave propagation time delay of 32.11 ms under 5% isoflurane (FIG. 7H), both in agreement with measurements made on respective time-domain, speckle contrast-based pulse wave signals (FIGS. 7E-7F).

Five arterial pulse waveforms under 2% isoflurane (FIG. 8A) and five arterial pulse waveforms under 5% isoflurane (FIG. 8B) were averaged to generate a mean speckle contrast-based flow waveform. The second derivative of each waveform is plotted to identify inflection points in the original waveform (FIGS. 8C, D). Cardiac parameters including systolic peak amplitude ($K_{systole}$), crest time (CT), diastolic peak amplitude ($K_{diastole}$), time to diastolic peak, time to dicrotic notch (DN) or the closure of the aortic valve, $K_b/K_a$ ratio, inflection point area (IPA) ratio ($A_2/A_1$), pulse duration, time between systolic and diastolic peak ($\Delta T$), and augmentation index (($K_{systole}-K_{diastole})/K_{systole}$) were quantified and are summarized in Table 1. Two-tailed student t-tests demonstrated significant changes in $K_{systole}$, $K_{diastole}$, time to diastolic peak, time to DN, IPA ratio, pulse duration, and $\Delta T$—consistent with the decreased heart rate, decreased cardiac output, decreased cardiac contractility, decreased peripheral vascular resistance, and delayed atrial filling expected in response to high-dose isoflurane anesthesia. No significant difference in CT, $K_b/K_a$ ratio, and augmentation index was observed between 2% and 5% isoflurane conditions.

Contents of each of related art references and/or articles identified in this disclosure is incorporated herein by reference.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Within this specification, embodiments have been described in a way that enables a clear and concise specification to bet written, but it is intended and will be appreciated that embodiments may be variously combined or separated without parting from the scope of the invention. In particular, it will be appreciated that all features described herein at applicable to all aspects of the invention.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The invention as recited in claims appended to this disclosure is intended to be assessed in light of the disclosure as a whole, including features disclosed in related art to which reference is made.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A method comprising:
operating a laser-speckle contrast imaging (LSCI) apparatus, which contains
an optical illumination system that has an optical axis and that includes a group of lenses and a set of optical apertures dimensioned to deliver light to the group of lenses in transmission of said light therethrough, and
an optical light-collecting system containing an optical detector and optically connected to the optical illumination system, wherein each of constituent apertures of the set of optical apertures is separated from the optical axis by a respectively corresponding non-zero distance,
by:
coupling a first illuminating light having a first optical parameter into an optical fiber component, configured to define said set of optical apertures, only through a first input facet area of the optical fiber component,
coupling a second illuminating light having a second optical parameter into said optical fiber component only through a second input facet area of the optical fiber component,
wherein the first and second input facet areas of the optical fiber component do not overlap with one another, and wherein the first and second optical parameters differ from one another;
forming, at a target surface, an optical image of the set of optical apertures in the first illuminating light delivered to the target surface through the set of optical apertures and through the group of lenses of the optical illumination system of the LSCI apparatus, wherein said optical image that has an image area that is
(15a) arcuate and curved around the optical axis; and/or
(15b) bound by two curved lines; and/or
(15c) annularly-shaped;
transmitting a portion of the first illuminating light from an object surface, that is separated from the optical illumination system by the target surface, towards an optical lens of the optical light collecting system of said LSCI apparatus through a designated area of the target surface while not transmitting said portion of the first illuminating light through the image area,
wherein the portion of said first illuminating light is formed by the illuminating light reflected at the object surface,
wherein said transmitting the portion of the first illuminating light through the designated area of the target surface includes transmitting said portion of the first illuminating light through a surface area, of the target surface, that is fully encircled by the image area of the optical image of the set of optical apertures;
and
forming at least one optical image of the object surface at an optical detector of the optical light-collecting system.

2. A method according to claim 1,
wherein said forming the optical image of the set of optical apertures includes receiving, by the group of lenses of the optical illumination system, of the first illuminating light having a first state of polarization,
wherein said transmitting includes transmitting the portion of said first illuminating light having a second state of polarization, and
wherein the first state of polarization and the second state of polarization are different from one another.

3. A method according to claim 1, further comprising mutually aligning the optical illumination system and the target surface by transmitting, through the set of optical apertures, the second illuminating light.

4. A method according to claim 3, wherein the first optical parameter and the second optical parameter include, respectively,
(18a) first and second optical wavelengths; and/or
(18b) first and second degrees of coherence; and/or
(18c) first and second polarizations.

5. A method according to claim 4, wherein, when the first optical parameter and the second optical parameter include, respectively, first and second degrees of coherence, the first degree of coherence is higher than the second degree of coherence.

6. A method according to claim 1 further comprising
transmitting said first illuminating light through at least one output facet of the optical fiber component, wherein the at least one output facet is dimensioned as a ring and defined in a surface transverse to an axis of the optical fiber component.

7. A method according claim 1, comprising:
during said operating, not receiving light from the set of optical apertures at an axial point of a first lens surface of the group of lenses, wherein the first lens surface is immediately neighboring to the set of optical apertures.

8. A method according to claim 1, wherein said operating comprises operating the LSCI apparatus in which
(23a) the set of optical apertures includes first and second optical aperture areas that are positioned at different azimuthal angles with respect to the optical axis in a plane substantially perpendicular to the optical axis; and/or
(23b) the set of optical apertures includes an array of optical apertures that is curved around the optical axis; and/or
(23c) the set of optical apertures includes an optical aperture shaped as a curved strip;
(23d) the set of optical apertures form an optical aperture ring surrounding the optical axis.

9. A method according to claim 7, further comprising:
substantially completely illuminating at least one output facet of the optical fiber component with at least one of the first illuminating light and the second illuminating light.

10. A method according to claim 1, wherein said coupling the first illuminating light and said coupling the second illuminating light is carried out either simultaneously or in a time-multiplexed fashion.

11. A method according to claim 1, further comprising:
with the use of a programmable data-processing electronic circuitry, operably connected with the optical detector, determining an index of motion at the object surface based at least in part on a speckle contrast characteristic of at least said optical image of the object surface formed with the use of the optical light-collecting system.

12. A method according to claim 11, wherein said determining an index of motion at the object surface includes determining the index of motion at a surface of a biological tissue, wherein said index of motion is a parameter of a blood flow in said biological tissue.

13. A method according to claim 11,
wherein the object surface is a surface of the retina of an eye, and
wherein said determining an index of motion includes:
(28a) determining a blood flow rate in a reference blood-vessel in said retina from the at least said optical image of the object surface; and
generating a visually-perceivable output representing quantified changes in retinal hemodynamics over a predetermined period of time based at least on said determining; and/or
(28b) ascertaining at least one of cardiac parameters including systolic peak amplitude, crest time, diastolic peak amplitude, time to diastolic peak, time to closure of an aortic valve, time between systolic and diastolic peaks, and augmentation index based on the at least said optical image of the object surface, and generating a visually-perceivable output representing said at least one of cardiac parameters.

14. A method according to claim 1, wherein at least one of the following conditions is satisfied:
(29a) said forming the at least one optical image of the object surface at the optical detector includes forming the at least one optical image in fluorescent light received from the object surface;
(29b) the method further comprises obtaining spectroscopic information about the object surface without establishing contact with said object surface; and
(29c) when the object surface is a surface of a biological tissue, the method further comprises determining a degree of blood oxygenation in the biological tissue without establishing contact with said biological tissue.

15. A method according to claim 1,
wherein the LSCI apparatus further includes a first auxiliary optical lens separated from the set of apertures by the group of lenses, wherein the optical illumination system and the optical light-collecting system share said first auxiliary optical lens, and
further comprising:
collecting a portion of light, that has been delivered through the set of optical apertures and through the group of lenses to the target surface and that has been reflected by the object surface separated from the group of lenses by the target surface, through an axial region of the target surface that substantially does not overlap with said image area of the optical image formed at the target surface.

16. A method according to claim 1, wherein the optical light-collecting system is configured to be polarizationally decoupled from the optical illumination system.

17. A method according to claim 1, comprising delivering the first illuminating light to the target surface through the set of optical apertures that is necessarily formed by the optical fiber component having at least one output optical fiber facet facing the group of lenses.

18. A method according to claim 17,
further comprising transmitting, through the set of optical apertures, the second illuminating light towards the target surface,
wherein an input facet of the optical fiber component is represented by the first and second input facet areas that are spatially distinct;
wherein the first illuminating light delivered to the target surface from a first source of light is collected by the optical fiber component only through the first input facet area, and the second illuminating light delivered to the target area from a second source of light is collected by the optical fiber component only through the second facet area, and
wherein the optical fiber component is structured
(35a) to substantially fully spatially overlap the first illuminating light and the second illuminating light upon propagation through the optical fiber component towards the at least one output facet of the optical fiber component to substantially completely illuminate said at least one output facet of the optical fiber component with either the first illuminating light or the second illuminating light or both the first and second illuminating lights; or
(35b) to substantially completely spatially separate the first illuminating light and the second illuminating light upon propagation through the optical fiber component towards at least one output facet of the optical fiber component to illuminate only a first subset of such at least one output facet of the optical fiber component with the first illuminating light, and only a second subset of such at least one output facet of the optical fiber component with the second illuminating light, the first and second subsets of the at least one output facet of the optical fiber components being spatially distinct from one another.

19. A method according to claim 17,
wherein said transmitting the first illuminating light includes transmitting the first illuminating light from a first source of light and
further comprising transmitting, through the set of optical apertures, a second illuminating light from a second source of light towards the target surface,
wherein:
(36a) the optical fiber component and the first source of light are configured to have the first illuminating light at the at least one output facet of the optical fiber component to maintain a degree of coherence that is higher than a pre-determined value despite and regardless of modal dispersion acquired by the first illuminating light upon propagation of said first illuminating light through the optical fiber component; and/or
(36b) the first and second sources of light are configured to operate either simultaneously or in a time-multiplexed fashion.

20. A method according to claim 1, further comprising: altering light distribution of the optical image formed at the target surface by varying an optical parameter of or varying a position of an element of the optical illumination system.

\* \* \* \* \*

UNITED STATES PATENT AND TRADEMARK OFFICE
CERTIFICATE OF CORRECTION

PATENT NO. : 11,974,812 B2
APPLICATION NO. : 18/550776
DATED : May 7, 2024
INVENTOR(S) : Dwani Patel et al.

It is certified that error appears in the above-identified patent and that said Letters Patent is hereby corrected as shown below:

In the Specification

Column 18, Line 5, "Index" should be --Iridex--.

Column 19, Line 46, "1 ms and exposure" should be --1 ms and 5 ms exposure--.

In the Claims

Claim 13, Column 29, Line 53, "determining; and/or" should be --determining the index of motion; and/or--.

Signed and Sealed this
Second Day of July, 2024

Katherine Kelly Vidal
*Director of the United States Patent and Trademark Office*